(12) United States Patent
Green

(10) Patent No.: US 9,974,300 B2
(45) Date of Patent: May 22, 2018

(54) YIELD ENHANCEMENT FOR STRESS-SUSCEPTIBLE PLANTS

(71) Applicant: AgroFresh Inc., Collegeville, PA (US)

(72) Inventor: Alan Ward Green, Des Moines, IA (US)

(73) Assignee: Agrofresh Inc., Collegeville, PA (US)

( * ) Notice: Subject to any disclaimer, the term of this patent is extended or adjusted under 35 U.S.C. 154(b) by 0 days. days.

(21) Appl. No.: 14/435,096

(22) PCT Filed: Oct. 11, 2013

(86) PCT No.: PCT/US2013/064432
§ 371 (c)(1),
(2) Date: Apr. 10, 2015

(87) PCT Pub. No.: WO2014/059209
PCT Pub. Date: Apr. 17, 2014

(65) Prior Publication Data
US 2015/0272115 A1 Oct. 1, 2015

Related U.S. Application Data

(60) Provisional application No. 61/712,412, filed on Oct. 11, 2012.

(51) Int. Cl.
*A01N 25/00* (2006.01)
*A01N 27/00* (2006.01)
*A01N 25/28* (2006.01)

(52) U.S. Cl.
CPC ............. *A01N 27/00* (2013.01); *A01N 25/28* (2013.01)

(58) Field of Classification Search
CPC ................................. A01N 27/00; A01N 25/28
See application file for complete search history.

(56) References Cited

U.S. PATENT DOCUMENTS

2007/0265166 A1* 11/2007 Bardella ............... A01N 27/00
504/357

FOREIGN PATENT DOCUMENTS

| EP | 1856976 A2 | 11/2007 |
|---|---|---|
| WO | 2009073211 A1 | 6/2009 |
| WO | 2011156388 A1 | 12/2011 |

OTHER PUBLICATIONS

Zheng, Jun, et al. "Genome-wide transcriptome analysis of two maize inbred lines under drought stress." Plant molecular biology 72.4-5 (2010): 407-421.*
Hunter, R. B., C. G. Mortimore, and L. W. Kannenberg. "Inbred maize performance following tassel and leaf removal." Agronomy Journal 65.3 (1973): 471-472.*
International Search Report dated Apr. 23, 2014 in PCT/US2013/064432 filed on Oct. 11, 2013.
Green et al., "Response of Corn (*Zea mays* L.) Inbreds and Hybrids to Sulfonylurea Herbicides", Weed Science, vol. 4, 1993, pp. 508-516.

* cited by examiner

*Primary Examiner* — Alton N Pryor
(74) *Attorney, Agent, or Firm* — Barnes & Thornburg LLP

(57) ABSTRACT

This invention is based on the use of cyclopropene to stabilize/enhance yield/seed production for corn inbred lines known to be stress-susceptible. Inbred corn lines are especially susceptible to environmental and mechanical stresses. Provided are methods and use of cyclopropene to enhance production of inbred seed from inbreds especially susceptible to stress. Also provided are methods and use of cyclopropene to enhance production of hybrid seed from inbreds susceptible to environmental stress. Also provided are methods and use of cyclopropene to enhance production of hybrid seed from inbreds susceptible to mechanical stress.

20 Claims, 15 Drawing Sheets

YIELD ENHANCEMENT FOR STRESS-SUSCEPTIBLE PLANTS

BACKGROUND OF THE INVENTION

Plants are often treated by contacting them with compositions. For example, U.S. patent application Ser. No. 11/324,617 discloses treating non-citrus plants with compositions that contain at least one cyclopropene and that contain at least one plant growth regulator that is not a cyclopropene. It is desired to provide methods that involve treating certain specific crop plants at developmental stage or stages appropriate for those specific crop plants. Independently, it is also desired to provide methods of treating plants that result in an increase in the yield of the crop produced by those plants.

Many inbred corn lines are especially susceptible to heat stress during early tassel formation and pollination. Other inbred corn lines are especially susceptible to drought stress during early to mid vegetative growth periods. Inbreds are also susceptible to the stress associated with the physical injury that occurs during the act of detasseling inbreds to be used as females. All of these situations result in exaggerated economic losses due to the weak nature of the inbreds and high value seed they produce.

Thus, there remains a need for methods to enhance yield or seed production for stress-susceptible plant, including certain inbred corn lines.

SUMMARY OF THE INVENTION

This invention is based on the use of cyclopropene to stabilize/enhance yield/seed production for corn inbred lines known to be stress-susceptible. Inbred corn lines are especially susceptible to environmental and mechanical stresses. Provided are methods and use of cyclopropene to enhance production of inbred seed from inbreds especially susceptible to stress. Also provided are methods and use of cyclopropene to enhance production of hybrid seed from inbreds susceptible to environmental stress. Also provided are methods and use of cyclopropene to enhance production of hybrid seed from inbreds susceptible to mechanical stress.

In one aspect, provided is method for improving the yield of a crop produced by a plurality of plants. The method comprises contacting said plants with a composition that comprises at least one cyclopropene compound, wherein the contacting is performed while the plants are in a location other than in a building, and the crop is susceptible to stress.

In one embodiment, the location comprises an open field. In another embodiment, the location does not comprise an enclosed environment. In a further embodiment, the enclosed environment is a container or a greenhouse.

In one embodiment, the composition is a liquid. In another embodiment, the composition comprises a complex of a cyclopropene compound and a molecular encapsulating agent. In another embodiment, the at least one cyclopropene compound comprises 1-methylcyclopropene (1-MCP). In a further or alternative embodiment, the molecular encapsulating agent is selected from alpha-cyclodextrin, beta-cyclodextrin, gamma-cyclodextrin, or combinations thereof. In a further embodiment, the molecular encapsulating agent comprises alpha-cyclodextrin.

In one embodiment, the cyclopropene compound is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_{1-8}$ alkyl. In another embodiment, R is methyl.

In another embodiment, the cyclopropene compound is of the formula:

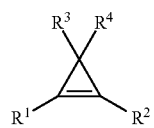

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cylcoalkylalkyl, phenyl, or napthyl group; and $R^2$, $R^3$, and $R^4$ are hydrogen.

In one embodiment, the stress comprises abiotic stress. Abiotic stress may include dehydration or other osmotic stress, salinity, high or low light intensity, high or low temperatures, submergence, exposure to heavy metals, and oxidative stress. In another embodiment, the stress comprises an environmental stress. In a further embodiment, the environmental stress comprises drought and/or heat. In another embodiment, the stress comprises mechanical stress.

In one embodiment, the crop comprises an inbred corn line. In another embodiment, the contacting is performed during tassel formation and/or pollination of the crop. In another embodiment, the contacting is performed during early to mid vegetative growth periods of the crop. In another embodiment, the yield comprises seed production. In another embodiment, the yield may be improved at least 10%; from 10% to 25%; from 10% to 30%; from 10% to 50%; from 20% to 40%, or from 20% to 50%.

DETAILED DESCRIPTION OF THE INVENTION

Figure 1:
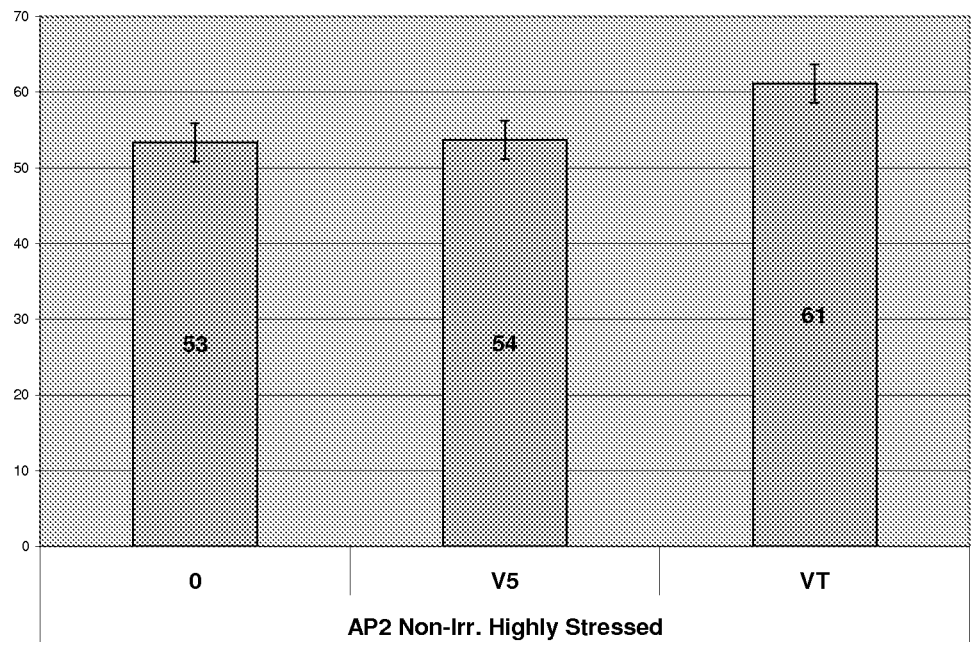
FIG. 1 shows a representative saleable units versus treatment at AP2 (stressed location). While not statistically significant, there are nearly 15% increase saleable units obtained from the VT application of AFxRD-038 at AP2.

The practice of the present invention involves the use of one or more cyclopropenes. As used herein, a cyclopropene compound means any compound with the formula

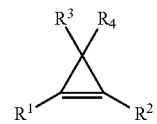

where each $R^1$, $R^2$, $R^3$ and $R^4$ is independently selected from the group consisting of H and a chemical group of the formula:

where n is an integer from 0 to 12; each L is independently selected from the group consisting of D1, D2, E, and J; where D1 is of the formula:

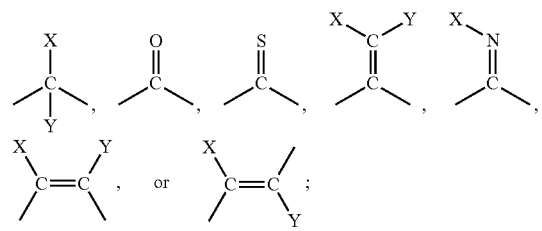

where D2 is of the formula:

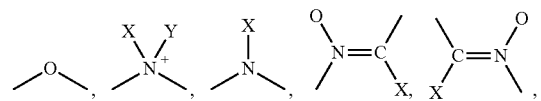

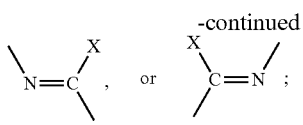

where E is of the formula:

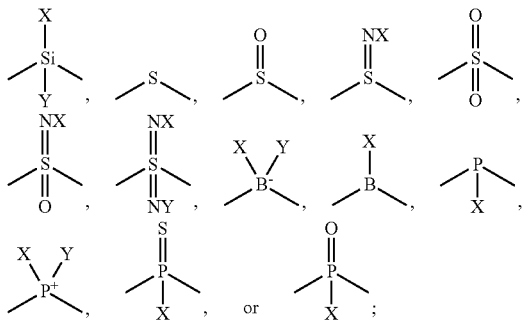

and
where J is of the formula:

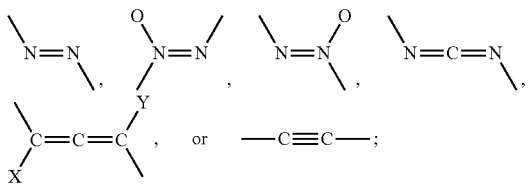

where each X and Y is independently a chemical group of the formula;

-(L)$_m$-Z;

and m is an integer from 0 to 8; and no more than two D2 or E groups are adjacent to each other and no J groups are adjacent to each other; where each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system; where the total number of heteroatoms in -(L)$_n$-Z is from 0 to 6; and where the total number of non-hydrogen atoms in the compound is 50 or less.

For the purposes of this invention, in the structural representations of the various L groups, each open bond indicates a bond to another L group, a Z group, or the cyclopropene moiety. For example, the structural representation

indicates an oxygen atom with bonds to two other atoms; it does not represent a dimethyl ether moiety.

Among embodiments in which at least one of $R^1$, $R^2$, $R^3$, and $R^4$ is not hydrogen and has more than one L group, the L groups within that particular $R^1$, $R^2$, $R^3$, or $R^4$ group may be the same as the other L groups within that same $R^1$, $R^2$, $R^3$, or $R^4$ group, or any other L groups within that same $R^1$, $R^2$, $R^3$, or $R^4$ group.

Among embodiments in which at least one of $R^1$, $R^2$, $R^3$, and $R^4$ contains more than one Z group, the Z groups within that $R^1$, $R^2$, $R^3$, or $R^4$ group may be the same as the other Z groups within that $R^1$, $R^2$, $R^3$, or $R^4$ group, or any number of Z groups within that $R^1$, $R^2$, $R^3$, or $R^4$ group may be different from the other Z groups within that $R^1$, $R^2$, $R^3$, or $R^4$ group.

The $R^1$, $R^2$, $R^3$, and $R^4$ groups are independently selected from the suitable groups. The $R^1$, $R^2$, $R^3$, and $R^4$ groups may be the same as each other, or any number of them may be different from the others. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted. Independently, groups that are suitable for use as one or more of $R^1$, $R^2$, $R^3$, and $R^4$ may be connected directly to the cyclopropene ring or may be connected to the cyclopropene ring through an intervening group such as, for example, a heteroatom-containing group.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be substituted or unsubstituted. Some suitable substituted aliphatic groups include, for example, acetylaminoalkenyl, acetylaminoalkyl, acetylaminoalkynyl, alkoxyalkoxyalkyl, alkoxyalkenyl, alkoxyalkyl, alkoxyalkynyl, alkoxycarbonylalkenyl, alkoxycarbonylalkyl, alkoxycarbonylalkynyl, alkylcarbonyloxyalkyl, alkyl (alkoxyimino)alkyl, carboxyalkenyl, carboxyalkyl, carboxyalkynyl, haloalkoxyalkenyl, haloalkoxyalkyl, haloalkoxyalkynyl, haloalkenyl, haloalkyl, haloalkynyl, hydroxyalkenyl, hydroxyalkyl, hydroxyalkynyl, trialkylsilylalkenyl, trialkylsilylalkyl, trialkylsilylalkynyl, dialkylaminoalkyl, alkylsulfonylalkyl, alkylthioalkenyl, alkylthioalkyl, alkylthioalkynyl, haloalkylthioalkenyl, haloalkylthioalkyl, and haloalkylthioalkynyl.

Also among the suitable $R^1$, $R^2$, $R^3$, and $R^4$ groups are, for example, substituted and unsubstituted aliphatic-oxy groups, such as, for example, alkenoxy, alkoxy, alkynoxy, and alkoxycarbonyloxy.

Also among the suitable $R^1$, $R^2$, $R^3$, and $R^4$ groups are, for example, substituted and unsubstituted alkylphosphonato, substituted and unsubstituted alkylphosphato, substituted and unsubstituted alkylamino, substituted and unsubstituted alkylsulfonyl, substituted and unsubstituted alkylcarbonyl, and substituted and unsubstituted alkylaminosulfonyl, including, for example, alkylphosphonato, dialkylphosphato, dialkylthiophosphato, dialkylamino, alkylcarbonyl, and dialkylaminosulfonyl.

Among the aliphatic groups suitable as $R^1$, $R^2$, $R^3$, or $R^4$ are, for example, cycloaliphatic groups, including, for example, cycloalkenyl, cycloalkyl, and cycloalkynyl. Suitable cycloaliphatic groups may be substituted or unsubstituted. Among the suitable substituted cycloaliphatic groups are, for example, acetylaminocycloalkenyl, acetylaminocycloalkyl, acetylaminocycloalkynyl, cycloalkenoxy, cycloalkoxy, cycloalkynoxy, alkoxyalkoxycycloalkyl, alkoxycycloalkenyl, alkoxycycloalkyl, alkoxycycloalkynyl, alkoxycarbonylcycloalkenyl, alkoxycarbonylcycloalkyl, alkoxycarbonylcycloalkynyl, cycloalkylcarbonyl, alkylcarbonyloxycycloalkyl, carboxycycloalkenyl, carboxycycloalkyl, carboxycycloalkynyl, halocycloalkoxycycloalkenyl, halocycloalkoxycycloalkyl, halocycloalkoxycycloalkynyl, halocycloalkenyl, halocycloalkyl, halocycloalkynyl, hydroxycycloalkenyl, hydroxycycloalkyl, hydroxycycloalkynyl, trialkylsilylcycloalkenyl, trialkylsilylcycloalkyl, trialkylsilylcycloalkynyl, dialkylaminocycloalkyl, alkylsulfonylcycloalkyl, cycloalkylcarbonyloxyalkyl, cycloalkylsulfonylalkyl, alkylthiocycloalkenyl, alkylthiocycloalkyl, alkylthiocycloalkynyl, haloalkylthiocycloalkenyl, haloalkylthiocycloalkyl, and haloalkylthiocycloalkynyl.

Also among the suitable $R^1$, $R^2$, $R^3$, and $R^4$ groups are, for example, substituted and unsubstituted cycloalkylsulfonyl groups and cycloalkylamino groups, such as, for example, dicycloalkylaminosulfonyl and dicycloalkylamino.

Also among the suitable $R^1$, $R^2$, $R^3$, and $R^4$ groups are, for example, substituted and unsubstituted heterocyclyl groups (i.e., non-aromatic cyclic groups with at least one heteroatom in the ring). Among the suitable substituted heterocyclyl groups are, for example, alkenylheterocyclyl, alkylheterocyclyl, alkynylheterocyclyl, acetylaminoheterocyclyl, alkoxyalkoxyheterocyclyl, alkoxyheterocyclyl, alkoxycarbonylheterocyclyl, alkylcarbonyloxyheterocyclyl, carboxyheterocyclyl, haloalkoxyheterocyclyl, haloheterocyclyl, hydroxyheterocyclyl, trialkylsilylheterocyclyl, dialkylaminoheterocyclyl, alkylsulfonylheterocyclyl, alkylthioheterocyclyl, heterocyclylthioalkyl, and haloalkylthioheterocyclyl.

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted aryl groups. Some suitable substituted aryl groups are, for example, alkenylaryl, alkylaryl, alkynylaryl, acetylaminoaryl, aryloxy, alkoxyalkoxyaryl, alkoxyaryl, alkoxycarbonylaryl, arylcarbonyl, alkylcarbonyloxyaryl, carboxyaryl, diarylamino, haloalkoxyaryl, haloaryl, hydroxyaryl, trialkylsilylaryl, dialkylaminoaryl, alkylsulfonylaryl, arylsulfonylalkyl, alkylthioaryl, arylthioalkyl, diarylaminosulfonyl, and haloalkylthioaryl.

Also among the suitable $R^1$, $R^2$, $R^3$, and $R^4$ groups are, for example, substituted and unsubstituted heteroaryl groups. Some suitable substituted heteroaryl groups are, for example, alkenylheteroaryl, alkylheteroaryl, alkynylheteroaryl, acetylaminoheteroaryl, heteroaryloxy, alkoxyalkoxyheteroaryl, alkoxyheteroaryl, alkoxycarbonylheteroaryl, heteroarylcarbonyl, alkylcarbonyloxyheteroaryl, carboxyheteroaryl, diheteroarylamino, haloalkoxyheteroaryl, haloheteroaryl, hydroxyheteroaryl, trialkylsilylheteroaryl, dialkylaminoheteroaryl, alkylsulfonylheteroaryl, heteroarylsulfonylalkyl, alkylthioheteroaryl, and haloalkylthioheteroaryl.

Also among the suitable $R^1$, $R^2$, $R^3$, and $R^4$ groups are, for example, substituted and unsubstituted heteroaryl groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring sysytems suitable as chemical group G may be monocyclic, bicyclic, tricyclic, polycyclic, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated 3 membered ring, such as, for example, a substituted or unsubstituted cyclopropane, cyclopropene, epoxide, or aziridine ring.

In some embodiments, G is a ring system that contains a 4 membered heterocyclic ring; in some of such embodiments, the heterocyclic ring contains exactly one heteroatom. Independently, in some embodiments, G is a ring system that contains a heterocyclic ring with 5 or more members; in some of such embodiments, the heterocyclic ring contains 1 to 4 heteroatoms. Independently, in some embodiments, the ring in G is unsubstituted; in other embodiments, the ring system contains 1 to 5 substituents; in some of the embodiments in which G contains substituents, each substituent is independently chosen from chemical groups in the category X as defined herein below. Also suitable are embodiments in which G is a carbocyclic ring system.

Among the suitable G groups are, for example, cyclopropyl, cyclobutyl, cyclopent-3-en-1-yl, 3-methoxycyclohexan-1-yl, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 2-iodo-4-methylphenyl, pyridin-2-yl, pyridin-3-yl, pyridin-4-yl, pyrazinyl, pyrimidin-2-yl, pyrimidin-4-yl, pyrimidin-5-yl, pyridazinyl, triazol-1-yl, imidazol-1-yl, thiophen-2-yl, thiophen-3-yl, furan-2-yl, furan-3-yl, pyrrolyl, oxazolyl, isoxazolyl, thiazolyl, isothiazolyl, oxadiazolyl, thiadiazolyl, quinolyl, isoquinolyl, tetrahydrofuryl, pyrrolidinyl, piperidinyl, tetrahydropyranyl, morpholinyl, piperazinyl, dioxolanyl, dioxanyl, indolinyl and 5-methyl-6-chromanyl, adamantyl, norbornyl, and their substituted analogs such as, for example: 3-butylpyridin-2-yl, 4-bromo-pyridin-2-yl, 5-carboethoxy-pyridin-2-yl, and 6-methoxyethoxy-pyridin-2-yl.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments include those embodiments, for example, in which G is unsubstituted or substituted phenyl, cyclopentyl, cycloheptyl, or cyclohexyl. In some of these embodiments, G is cyclopentyl, cycloheptyl, cyclohexyl, phenyl, or substituted phenyl. Among embodiments in which G is substituted phenyl are embodiments, for example, in which there are 1, 2, or 3 substituents. Independently, also among embodiments in which G is substituted phenyl are embodiments, for example, in which the substituents are independently selected from methyl, methoxy, and halo.

In some embodiments, one or more cyclopropenes are used in which one or more of $R^1$, $R^2$, $R^3$, and $R^4$ is hydrogen. In some embodiments, $R^1$ or $R^2$ or both $R^1$ and $R^2$ is hydrogen. Independently, in some embodiments, $R^3$ or $R^4$ or both $R^3$ and $R^4$ is hydrogen. In some embodiments, $R^2$, $R^3$, and $R^4$ are hydrogen.

In some embodiments, one or more of $R^1$, $R^2$, $R^3$, and $R^4$ is a structure that has no double bond. Independently, in some embodiments, one or more of $R^1$, $R^2$, $R^3$, and $R^4$ is a structure that has no triple bond. Independently, in some embodiments, one or more of $R^1$, $R^2$, $R^3$, and $R^4$ is a structure that has no halogen atom substituent. Independently, in some embodiments, one or more of $R^1$, $R^2$, $R^3$, and $R^4$ is a structure that has no substituent that is ionic. Independently, in some embodiments, one or more of $R^1$, $R^2$, $R^3$, and $R^4$ is a structure that is not capable of generating oxygen compounds.

In some embodiments of the invention, one or more of $R^1$, $R^2$, $R^3$, and $R^4$ is hydrogen or $(C_1-C_{10})$ alkyl. In some embodiments, each of $R^1$, $R^2$, $R^3$, and $R^4$ is hydrogen or $(C_1-C_8)$ alkyl. In some embodiments, each of $R^1$, $R^2$, $R^3$, and $R^4$ is hydrogen or $(C_1-C_4)$ alkyl. In some embodiments, each of $R^1$, $R^2$, $R^3$, and $R^4$ is hydrogen or methyl. When $R^1$ is methyl and each of $R^2$, $R^3$, and $R^4$ is hydrogen, the cyclopropene is known herein as "1-MCP."

In some embodiments, a cyclopropene is used that has boiling point at one atmosphere pressure of 50° C. or lower; or 25° C. or lower; or 15° C. or lower. Independently, in some embodiments, a cyclopropene is used that has boiling point at one atmosphere pressure of −100° C. or higher; −50° C. or higher; or −25° C. or higher; or 0° C. or higher.

The cyclopropenes applicable to this invention may be prepared by any method. Some suitable methods of preparation of cyclopropenes are the processes disclosed in U.S. Pat. Nos. 5,518,988 and 6,017,849. Any compound that is not a cyclopropene is known herein as a "non-cyclopropene."

In some embodiments, one or more composition of the present invention includes at least one ionic complexing reagent. An ionic complexing reagent interacts with a cyclopropene to form a complex that is stable in water. Some suitable ionic complexing reagents, for example, include lithium ion. In some embodiments, no ionic complexing reagent is used.

In some embodiments, no composition of the present invention includes any molecular encapsulating agent. In other embodiments, one or more composition of the present invention includes at least one molecular encapsulating agent.

When a molecular encapsulating agent is used, suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments of the invention, the encapsulating agent is alpha-cyclodextrin, beta-cyclodextrin, gamma-cyclodextrin, or a mixture thereof. In some embodiments of the invention, particularly when the cyclopropene is 1-methylcyclopropene, the encapsulating agent is alpha-cyclodextrin. The preferred encapsulating agent will vary depending upon the structure of the cyclopropene or cyclopropenes being used. Any cyclodextrin or mixture of cyclodextrins, cyclodextrin polymers, modified cyclodextrins, or mixtures thereof can also be utilized pursuant to the present invention. Some cyclodextrins are available, for example, from Wacker Biochem Inc., Adrian, Mich. or Cerestar USA, Hammond, Ind., as well as other vendors.

In some of the embodiments in which a molecular encapsulating agent is present, at least one molecular encapsulating agent encapsulates one or more cyclopropenes. A cyclopropene or substituted cyclopropene molecule encapsulated in a molecule of a molecular encapsulating agent is known herein as a "cyclopropene molecular encapsulating agent complex." The cyclopropene molecular encapsulation agent complexes can be prepared by any means. In one method of preparation, for example, such complexes are prepared by contacting the cyclopropene with a solution or slurry of the molecular encapsulation agent and then isolating the complex, using, for example, processes disclosed in U.S. Pat. No. 6,017,849. For example, in one method of making a complex in which 1-MCP is encapsulated in a molecular encapsulating agent, the 1-MCP gas is bubbled through a solution of alpha-cyclodextrin in water, from which the complex first precipitates and is then isolated by filtration. In some embodiments, complexes are made by the above method and, after isolation, are dried and stored in solid form, for example as a powder, for later addition to useful compositions.

In some embodiments, one or more molecular encapsulating agent and one or more cyclopropenes are both present in a composition; in some of such embodiments, the amount of molecular encapsulating agent can usefully be characterized by the ratio of moles of molecular encapsulating agent to moles of cyclopropene. In some embodiments, the ratio of moles of molecular encapsulating agent to moles of cyclopropene is 0.1 or larger; or 0.2 or larger; or 0.5 or larger; or 0.9 or larger. Independently, in some of such embodiments, the ratio of moles of molecular encapsulating agent to moles of cyclopropene is 2 or lower; or 1.5 or lower.

In some embodiments, the composition of the present invention has no abscission agent.

In the practice of the present invention, the composition may be contacted with a plant in a variety of ways. For example, the composition of the present invention may be a solid, a liquid, a gas, or a mixture thereof.

In some embodiments, a plant is contacted with at least one composition of the present invention that is a gas. Among such embodiments, it is contemplated that the plant being treated will be surrounded by a normal ambient atmosphere (at approximately 1 atmosphere pressure) to which composition of the present invention has been added. In some embodiments, the concentration of cyclopropene is 0.1 nl/l (i.e., nanoliter per liter) or higher; or 1 nl/l or higher, or 10 nl/l or higher; or 100 nl/l or higher. Independently, in some embodiments, the concentration of cyclopropene is 3,000 nl/l or lower; or 1,000 nl/l or lower.

In some embodiments, the practice of the present invention involves one or more liquid compositions. In some embodiments, liquid compositions are liquid at 25° C. In some embodiments, liquid compositions are liquid at the temperature at which the composition is used to treat plants. Because plants are often treated outside of any buildings, plants may be treated at temperatures ranging from 1° C. to 45° C.; suitable liquid compositions need not be liquid over that entire range, but suitable liquid compositions are liquid at some temperature from 1° C. to 45° C.

A liquid composition of the present invention may be a single pure substance, or it may contain more than one substance. If a liquid composition contains more than one substance, that liquid composition may be a solution or a dispersion or a combination thereof. If, in the liquid composition, one substance is dispersed in another substance in the form of a dispersion, the dispersion may be of any type, including, for example, a suspension, a latex, an emulsion, a miniemulsion, a microemulsion, or any combination thereof.

Among embodiments in which the composition of the present invention is a liquid, the amount of cyclopropene in the composition may vary widely, depending on the type of composition and the intended method of use. In some embodiments, the amount of cyclopropene, based on the total weight of the composition, is 4% by weight or less; or 1% by weight or less; or 0.5% by weight or less; or 0.05% by weight or less. Independently, in some embodiments, the amount of cyclopropene, based on the total weight of the composition, is 0.000001% by weight or more; or 0.00001% by weight or more; or 0.0001% by weight or more; or 0.001% by weight or more.

Among embodiments of the present invention that use a composition of the present invention that contains water, the amount of cyclopropene may be characterized as parts per million (i.e., parts by weight of cyclopropene per 1,000,000 parts by weight of water in the composition, "ppm") or as parts per billion (i.e., parts by weight of cyclopropene per 1,000,000,000 parts by weight of water in the composition, "ppb"). In some embodiments, the amount of cyclopropene is 1 ppb or more; or 10 ppb or more; or 100 ppb or more. Independently, in some embodiments, the amount of cyclopropene is 10,000 ppm or less; or 1,000 ppm or less.

In some embodiments, a composition of the present invention that is a liquid is used in which some or all of the cyclopropene is encapsulated in one or more encapsulating agent.

In some embodiments, no composition of the present invention includes one or more metal-complexing agents. In some embodiments, one or more compositions of the present invention include one or more metal-complexing agents.

Among embodiments in which one or more liquid compositions are used, in some of such embodiments, one or more metal-complexing agents may be included in one or more liquid compositions. A metal-complexing agent is a compound that is capable of forming coordinate bonds with metal atoms. Some metal-complexing agents are chelating agents. As used herein, a "chelating agent" is a compound, each molecule of which is capable of forming two or more coordinate bonds with a single metal atom. Some metal-complexing agents form coordinate bonds with metal atoms because the metal-complexing agents contain electron-donor atoms that participate in coordinate bonds with metal atoms. Suitable chelating agents include, for example, organic and inorganic chelating agents. Among the suitable inorganic chelating agents are, for example, phosphates such as, for example, tetrasodium pyrophosphate, sodium tripolyphosphate, and hexametaphosphoric acid. Among the suitable organic chelating agents are those with macrocyclic structures and non-macrocyclic structures. Among the suitable macrocyclic organic chelating agents are, for example, porphine compounds, cyclic polyethers (also called crown ethers), and macrocyclic compounds with both nitrogen and oxygen atoms.

Some suitable organic chelating agents that have non-macrocyclic structures are, for example, aminocarboxylic acids, 1,3-diketones, hydroxycarboxylic acids, polyamines, aminoalcohols, aromatic heterocyclic bases, phenol, aminophenols, oximes, Shiff bases, sulfur compounds, and mixtures thereof. In some embodiments, the chelating agent includes one or more aminocarboxylic acids, one or more hydroxycarboxylic acids, one or more oximes, or a mixture thereof. Some suitable aminocarboxylic acids include, for example, ethylenediaminetetraacetic acid (EDTA), hydroxyethylethylenediaminetriacetic acid (HEDTA), nitrilotriacetic acid (NTA), N-dihydroxyethylglycine (2-HxG), ethylenebis (hydroxyphenylglycine) (EHPG), and mixtures thereof. Some suitable hydroxycarboxylic acids include, for example, tartaric acid, citric acid, gluconic acid, 5-sulfosalicylic acid, and mixtures thereof. Some suitable oximes include, for example, dimethylglyoxime, salicylaldoxime, and mixtures thereof. In some embodiments, EDTA is used.

Some additional suitable chelating agents are polymeric. Some suitable polymeric chelating agents include, for example, polyethyleneimines, polymethacryloylacetones, poly(acrylic acid), and poly(methacrylic acid). Poly(acrylic acid) is used in some embodiments.

Some suitable metal-complexing agents that are not chelating agents are, for example, alkaline carbonates, such as, for example, sodium carbonate.

Metal-complexing agents may be present in neutral form or in the form of one or more salts. Mixtures of suitable metal-complexing agents are also suitable.

In some embodiments of the present invention, the compositions of the present invention do not contain water. In other embodiments, the compositions of the present invention contain water; in some of such embodiments, the water contains one or more metal ions, such as, for example, iron ions, copper ions, other metal ions, or mixtures thereof. In some embodiments, the water contains 0.1 ppm or more of one or more metal ions.

Among embodiments that use one or more metal-complexing agents, the amount of metal-complexing agent used may vary widely. In some embodiments in which at least one liquid composition is used, the amount of metal-complexing agent in that liquid composition will be adjusted to be sufficient to complex the amount of metal ion that is present or expected to be present in the liquid composition that contains the metal-complexing agent. For example, in some embodiments in which a liquid composition of the present invention is used that includes water that contains some metal ion, if a relatively efficient metal-complexing agent is used (i.e., a metal-complexing agent that will form a complex with all or nearly all the metal ions in the water), the ratio of moles of metal-complexing agent to moles of metal ion will be 0.1 or greater; or 0.2 or greater; or 0.5 or greater; or 0.8 or greater. Among such embodiments that use a relatively efficient metal-complexing agent, the ratio of moles of metal-complexing agent to moles of metal ion will be 2 or less; or 1.5 or less; or 1.1 or less. It is contemplated that, if a less-efficient metal-complexing agent is used, the ratio of moles of metal-complexing agent to moles of metal ion could be increased to compensate for the lower efficiency.

Independently, in some embodiments in which a liquid composition is used, the amount of metal-complexing agent is, based on the total weight of the liquid composition, 25% by weight or less; or 10% by weight or less; or 1% by weight or less. Independently, in some embodiments, the amount of metal-complexing agent is, based on the total weight of the liquid composition, 0.00001% or more; or 0.0001% or more; or 0.01% or more.

Independently, in some embodiments in which a liquid composition that includes water is used, the amount of metal-complexing agent can usefully be characterized by the molar concentration of metal-complexing agent in the water (i.e., moles of metal-complexing agent per liter of water). In some of such liquid compositions, the concentration of metal-complexing agent is 0.00001 mM (i.e., milli-Molar) or greater; or 0.0001 mM or greater; or 0.001 mM or greater; or 0.01 mM or greater; or 0.1 mM or greater. Independently, in some embodiments in which a liquid composition of the present invention includes water, the concentration of metal-complexing agent is 100 mM or less; or 10 mM or less; or 1 mM or less.

In some embodiments of the present invention, one or more adjuvants is also included in the composition of the present invention. The use of adjuvants is considered optional in the practice of the present invention. Adjuvants may be used alone or in any combination. When more than one adjuvant is used, it is contemplated that any combination of one or more adjuvants may be used. Some suitable adjuvants are surfactants, alcohols, oils, extenders, pigments, fillers, binders, plasticizers, lubricants, wetting agents, spreading agents, dispersing agents, stickers, adhesives, defoamers, thickeners, transport agents, and emulsifying agents.

In some embodiments, a composition of the present invention is used that contains at least one adjuvant selected from alcohols, oils, and mixtures thereof; such a composition may or may not additionally contain one or more surfactant.

Among embodiments in which one or more liquid compositions are used, various embodiments are contemplated that include the use of, for example, any one or more of the following liquid compositions: liquid compositions that contain one or more surfactant but no oil and no alcohol; liquid compositions that contain one or more oil but no surfactant and no alcohol; and liquid compositions that contain one or more alcohol but no surfactant and no oil. In some embodiments, one or more liquid compositions are used that each contain one or more surfactant and one or more oil; or one or more liquid compositions are used that each contain one or more surfactant and one or more alcohol. In some embodiments, one or more liquid compositions are used that each contains one or more surfactant, one or more oil, and one or more alcohol.

Among embodiments in which one or more liquid compositions are used, in some liquid compositions, one or more alcohols are used. Suitable alcohols include, for example, alkyl alcohols and other alcohols. As used herein, alkyl alcohols are alkyl compounds with one hydroxyl group; the alkyl group may be linear, branched, cyclic, or a combination thereof; the alcohol may be primary, secondary, or tertiary. In some embodiments, alkyl alcohols are used which have alkyl groups with 2 or more carbon atoms. In some embodiments, ethanol, isopropanol, or a mixture thereof is used. In some embodiments, one or more alkyl alcohols are used which have alkyl groups with 20 or fewer carbon atoms; or 10 or fewer carbon atoms; or 6 or fewer carbon atoms; or 3 or fewer carbon atoms.

Among liquid compositions that use alcohol, some liquid compositions use alcohol in amounts, by weight based on the total weight of the liquid composition, of 0.25% or higher; or 0.5% or higher; or 1% or higher. Among liquid compositions that use alcohol, some liquid compositions use alcohol in amounts, by weight based on the total weight of the liquid composition, of 90% or less; or 50% or less; or 10% or less; or 5% or less; or 4% or less; or 3% or less.

As used herein, the phrase "plant" includes dicotyledons plants and monocotyledons plants. Some plants are grown for the purpose of removing one or more plant parts, when such parts are considered a useful product. Such plants are known herein as "crop plants." Removal of such useful plant parts is known as harvesting. In the practice of the present invention, plants that produce useful plant parts are treated with composition of the present invention prior to the harvesting of the useful plant parts. In such embodiments, each composition that is used may, independently of any other compositions that may be used, be brought into contact with all of or with some portion of the plant. If a composition is brought into contact with a portion of the plant, that portion may or may not include the useful plant part intended to be harvested.

In the practice of the present invention, at least one treatment is performed on crop plants before any useful plant parts are harvested. The growth and development process of many crop plants can be described by certain developmental stages. For example, many crop plants develop through vegetative stages followed by reproductive stages. In some embodiments, crop plants are contacted with a composition of the present invention one or more times during one or more vegetative stages. Independently, in some embodiments, crop plants are contacted with a composition of the present invention one or more times during one or more reproductive stages. Also contemplated are embodiments in which crop plants are contacted with a composition of the present invention one or more times during one or more vegetative stages and also contacted with a composition of the present invention one or more times during one or more reproductive stages. Some crop plants develop through ripening stages after their reproductive stages; it is contemplated in some embodiments to contact such crop plants with one or more composition of the present invention one or more times during one or more ripening stage, either in addition to or instead of contact with one or more composition of the present invention during other stage or stages. In some embodiments, the plants or crop plants of the present invention include seed corn and inbred corn production.

Some crop plants develop through vegetative and reproductive processes simultaneously. It is contemplated to contact such crop plants with one or more composition of the present invention one or more times after germination but before harvest.

It is contemplated that, for some specific crop plants, there may be an optimum stage or stages at which to perform the contact with the composition of the present invention, in order to achieve the maximum improvement in crop yield. It is contemplated that such optimum stage or stages may be different for each type of crop plant, and such optimum stage or stages may, in some cases, depend on the specific growing conditions.

In some embodiments, it is contemplated to contact a group of crop plants at a certain desired stage of development. In such cases, it is contemplated that such contacting may be performed when the ratio of the number of plants that have reached the desired stage of development to the total number of plants in the group is at least 0.1, or at least 0.5, or at least 0.75, or at least 0.9 (i.e., when the portion of plants that have reached the desired stage of development is at least 10%, or 50%, or 75%, or 90%).

For example, corn plants also develop through vegetative stages followed by reproductive stages. The vegetative growth stages of corn plants include VE (emergence), V1 (emergence of first leaf), VN (emergence of Nth leaf), VNMAX (emergence of last leaf), and VT (tasselling). One of these vegetative stages is V5, which begins when the fifth leaf emerges. Another of these vegetative stages is V12, which begins when the twelfth leaf emerges. The reproductive growth stages of corn plants include R1 (silking), R2 (blister), R3 (milk), R4 (dough), R5 (dent), R6 (maturity). In some embodiments, corn plants are contacted with one or more composition of the present invention during or after any of V5 (emergence of fifth leaf), V12 (emergence of 12th leaf), VT, R3, or during or after any combination of two or more of V6, V12, VT, and R3. Independently, in some embodiments, corn plants are contacted with one or more composition of the present invention during V12, during VT, and during R3. Independently, some embodiments involve spraying corn plants one or more times with at least one liquid composition comprising at least one cyclopropene, after at least 10% of said corn plants have reached the developmental stage at which the fifth leaf is fully expanded, or after at least 10% of said corn plants have reached the developmental stage at which the twelfth leaf is fully expanded.

Suitable treatments may be performed on plants that are planted in a field, in a garden, in a building (such as, for example, a greenhouse), or in another location. Suitable treatments may be performed on a plants that are planted in open ground, in one or more containers (such as, for example, a pot, planter, or vase), in confined or raised beds, or in other places.

In some embodiments, treatment is performed on plants that are in a location other than in a building.

In some embodiments, plants are treated while they are growing in a container such as, for example, pots, flats, or portable beds. In some of such cases, when treated plants are subsequently transplanted to open ground, the treated plants resist the stress of transplantation better than untreated plants do. In some embodiments, such resistance to transplantation stress can lead to improved crop yield. For example, tomatoes that are treated according to the practice of the present invention and that are transplanted can sometimes show improved resistance to transplantation stress and, sometimes, improved crop yield, in comparison to untreated tomato plants.

In some embodiments, the amount of cyclopropene is chosen to be appropriate for the particular crop that is being treated. For example, in some of the embodiments in which the crop plants are corn or soybean, the amount of cyclopropene is 500 g/ha or less; or 250 g/ha or less; or 100 g/ha or less, or 50 g/ha or less. For another example, in some of the embodiments in which the crop plants are cotton, the amount of cyclopropene is 50 g/ha or more; or 100 g/ha or more; or 200 g/ha or more.

In some embodiments of the present invention, a group of plants is treated simultaneously or sequentially. One characteristic of such a group of plants is the crop yield, which is defined as the amount (herein called "crop amount") of useful plant parts collected from a defined group of plants. In one useful definition of the crop yield, the defined group of plants is the group that occupies a certain area of ground (this definition is often used when plants are growing in a contiguous group in a field). In another useful definition of the crop yield, the defined group of plants is a specific number of individually identified plants (this definition may be used for any group of plants, including, for example, plants in fields, in pots, in greenhouses, or any combination thereof).

The crop amount may be defined in a variety of ways. In the practice of the present invention, the crop amount may be measured, for example, by any of the following methods: weight, volume, number of harvested plant parts, or biomass. Also contemplated are methods in which the crop amount is measured as the amount in the crop of a specific constituent (such as, for example, sugar, starch, or protein). Further contemplated are methods in which the crop amount is measured as the amount of a certain characteristic (such as, for example, redness, which is sometimes used to measure the amount of a crop of tomatoes). Additionally contemplated are methods in which the crop amount is measured as the amount of a specific portion of the harvested plant part (such as, for example, the number of kernels or the weight of kernels, which are sometimes used to measure the amount of a crop of corn; or the weight of lint, which is sometimes used to measure the amount of a cotton crop).

In some embodiments, the crop yield is defined as the crop amount per unit of area of land. That is, the land area from which the crop was harvested is measured, and the crop amount is divided by the land area to calculate the crop yield. For example, a crop amount measured as the weight of harvested plant parts would lead to a crop yield that is reported as a weight per area (for example, kilograms per hectare).

It is contemplated that, in some embodiments, the harvested plant parts that contribute to the crop amount are those plant parts that meet the minimum quality criteria that are appropriate for that type of plant part. That is, when plant parts are harvested from certain plants, the crop amount is, for example, the weight of the plant parts of acceptable quality that are harvested from those plants. Acceptable quality may be determined by any of the common criteria used by persons who harvest or handle the plant part of interest. Such criteria of acceptable quality of a plant part may be, for example, one or more of size, weight, firmness, resistance to bruising, flavor, sugar/starch balance, color, beauty, other quality criteria, or any combination thereof. Also contemplated as a criterion of quality, either alone or in combination with any of the foregoing criteria, is the time over which the plant part maintains its quality (as judged by any of the forgoing criteria).

In some embodiments of the present invention, treatment of a group of plants with the methods of the present invention will increase the crop yield of that group of plants, compared to the crop yield that would have been obtained from that group of plants if it had not been treated with the methods of the present invention. The increase in crop yield may be obtained in any of a wide variety of ways. For example, one way an increase in crop yield may be obtained is that each plant may produce a greater number of useful plant parts. As another example, one way an increase in crop yield may be obtained is that each useful plant part may have higher weight. As a third example, crop yield may increase when a larger number of potentially useful plant parts meet the minimum criteria for acceptable quality. Other ways of increasing the crop yield may also result from the practice of the present invention. Also contemplated are increases in crop yield that happen by any combination of ways.

Another contemplated benefit of practicing some embodiments of the present invention is that the general quality of the crop may be improved. That is, a crop produced by methods of the present invention may have a general or average level of quality higher than comparable crops produced without the methods of the present invention, as judged by the quality criteria appropriate for that crop. In some cases, such higher-quality crops may command higher prices when sold.

The improvement in crop yield caused by the practice of the present invention may arise by any mechanism. That is, the practice of the present invention, in some embodiments, may cause an improvement in some process of the plant's development, maturation, growth, or reproduction, and such improvement in such process may, in turn, cause improvement in crop yield. For example, the practice of the present invention may cause an improvement in any one or any combination of the following processes: synchronization of pollination (i.e., better agreement between the time period when a plant sheds pollen and the time period when that plant is able to receive the pollen and become fertilized), photosynthesis, nitrogen accumulation, leaf senescence, or late-season production of green leaves. In some of the embodiments where photosynthesis is improved, the improvement in photosynthesis can be observed as increased assimilation of carbon dioxide. Independently, the improvement in crop yield may, in some embodiments, occur because of improvement in disease resistance or drought resistance or frost resistance or heat resistance or a combination thereof.

In some crops (such as, for example, corn), it is contemplated that drought resistance and the resultant improvement in crop yield arise because the practice of the present invention causes stomatal closure, which gives the plant its resistance to drought. Independently, some crops (such as, for example, wheat) experience improved frost tolerance when used in the practice of the present invention. Independently, some crops (such as, for example, wheat and grapes) experience improved resistance to disease when used in the practice of the present invention.

In some embodiments, improvement in crop yield may occur because of a delay in the dropping of one or more of leaves, flowers, or fruiting structures (such as, for example, pods, bolls, or the fruit itself). In some embodiments, improvement in crop yield may occur because of enhanced root nodulation, which sometimes occurs in certain crops such as, for example, soybeans.

Whether or not the practice of the present invention results in improvement in one or more of the above-mentioned processes, in some embodiments the practice of the present invention leads to improvement in one or more of the following: biomass volume, biomass quality, increased fruit, increased fruit size (when desired), decreased fruit size (when desired), harvest timing (advanced or delayed, as desired), reduced fruit drop, decreased cell turgor, decreased russetting, lowered stress response, lowered wounding response, reduced storage disorders in harvested plant parts, increased shelf life of harvested plant parts, apical dominance, abscission prevention, senescence prevention, yellowing prevention, improved vigor during growth, improved vigor during transit, improved vigor during transplant, and combinations thereof.

In some embodiments, an improvement in crop yield is evident at the time of harvest, such as, for example, when the improvement is an increase in weight of crop per unit area of land. In some embodiments, an improvement in crop yield is observed some time after the crop has been in storage. That is, in some cases, the crop yield is measured as the amount of high-quality crop that is delivered to the retail market after storage. It is contemplated that some embodiments of the present invention involve pre-harvest contacting of crop plants resulting in crop that can be put in storage after harvest and then come out of storage with higher quality than previously obtainable.

EXAMPLES

Example 1

A representative saleable units versus treatment at AP2 (stressed location) is shown in FIG. 1. While not statistically significant, there are nearly 15% increase saleable units obtained from the VT application of AFxRD-038 at AP2.

Figure 2:
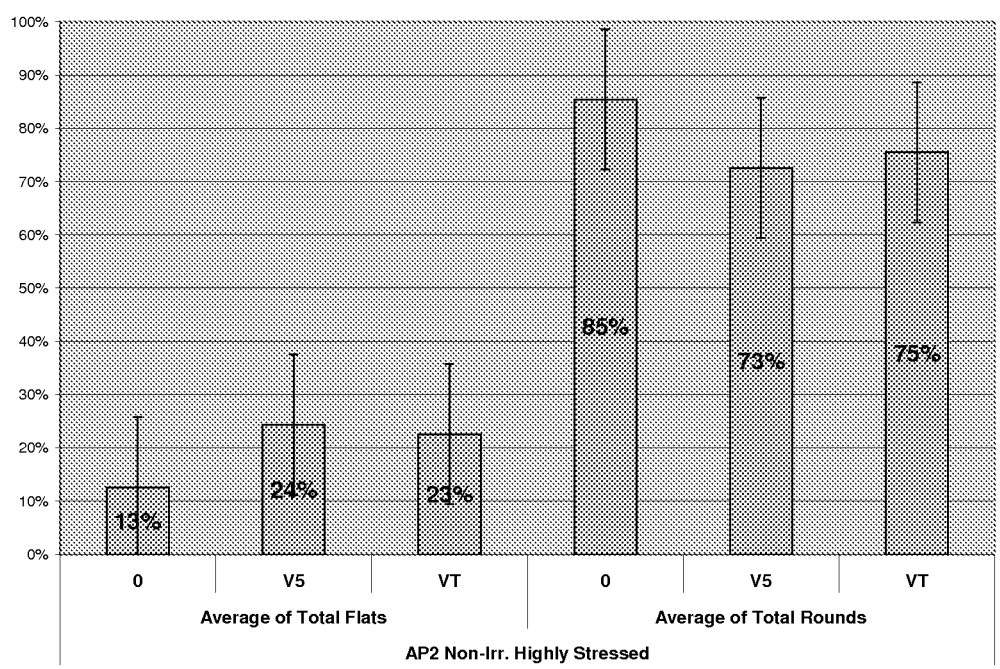
FIG. 2 shows a representative comparison of Flats versus Rounds within the AP2 location. While not statistically significant, there is a trend toward increased percentage of flat seeds with application of AFxRD-038.

A representative comparison of Flats versus Rounds within the AP2 location is shown in FIG. 2. While not statistically significant, there is a trend toward increased percentage of flat seeds with application of AFxRD-038.

There are no visible phytotoxic effects observed from the applications of AFxRD-038 in any of the plots.

There are significant differences in almost all of the seed traits due to location but no statistically significant differences related to treatment. The more stressed location, AP2, resulted in lower yield and fewer, smaller and flatter seeds with slightly lower germination.

There are trends towards more flat seeds and more saleable units of seed produced per acre (~15%) with the VT application of AFxRD-038 at the AP2 location. The increase in saleable units appears to be a result of more flats and fewer large round seeds.

Example 2

A similar experiment showing effects of AFxRD-038 in hybrid seed corn product is conducted and results are summarized in FIGS. 3-10. The Objective of this study is to determine whether applications of AFxRD-038 have a positive effect on seed yield of hybrid seed production.

Treatments with AFxRD-038 in hybrid seed production indicate that there is potential for increased value with little risk of phytotoxic or detrimental effects. Increased value seems to be possible from increased seeds per acre under stressed production conditions. Treatments used are the following:

(1) AFxRD-038 @ 25 gm/ha, V5
(2) AFxRD-038 @ 25 gm/ha, VT (just prior to detasseling)
(3) UTC 2 Replications, Plots 15 ft (4 rows female+2 rows male)× 50 feet long Observations include the following parameters: Phytotoxicity, Chlorosis, Necrosis, Plant Height Reduction, Date of Anthesis & Silking versus UTC, Leaf Senescence, % Barren stalks, Yield, % Moisture, # Kernel Rows, Test Weight, 1000 Seed Weight, Seed Size Distribution, and Germination (warm, cold and advanced aging).

Locations include (1) AP1: Essentially non-stressed, irrigated; and (2) AP2: Highly stressed non-irrigated.

No negative effects of product application are observed in any of the treatments at either location. No differences in flowering characteristics are observed (date of pollination, date of silking), and no differences in crop maturation are observed.

Figure 3A:
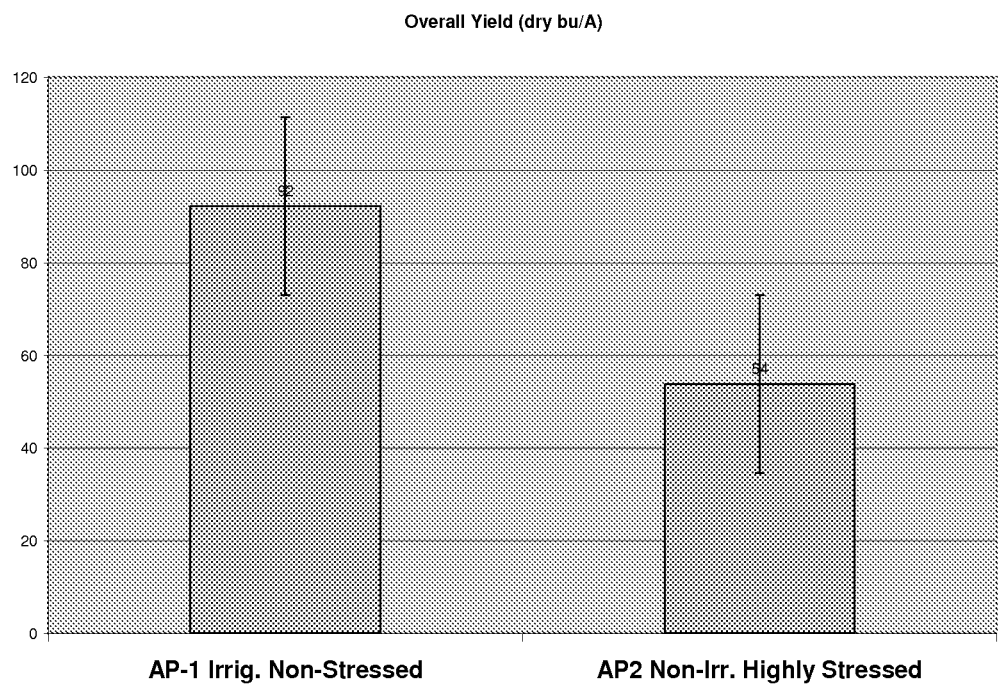
FIG. 3A shows a representative yield comparison of trial locations. Overall yield of AP2 is significantly reduced due to environmental and biotic stresses during the season. AP2 experienced drought and high temperatures, hail damage and subsequent Japanese beetle infestations. Grain yield at AP1 is very respectable for a seed production field and is enhanced through timely irrigation.
Figure 3B:
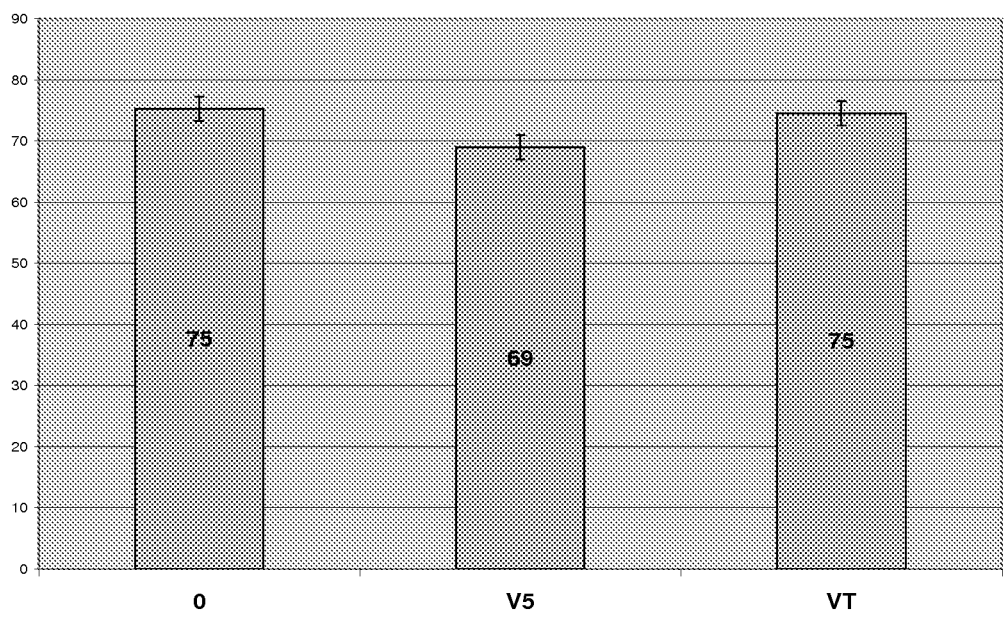
FIG. 3B shows a representative yield comparison of treatments across AP1 and AP2 locations. Data combined across locations indicate some overall yield reduction though not statistically significant in plots treated compared to the UTC.
Figure 3C:
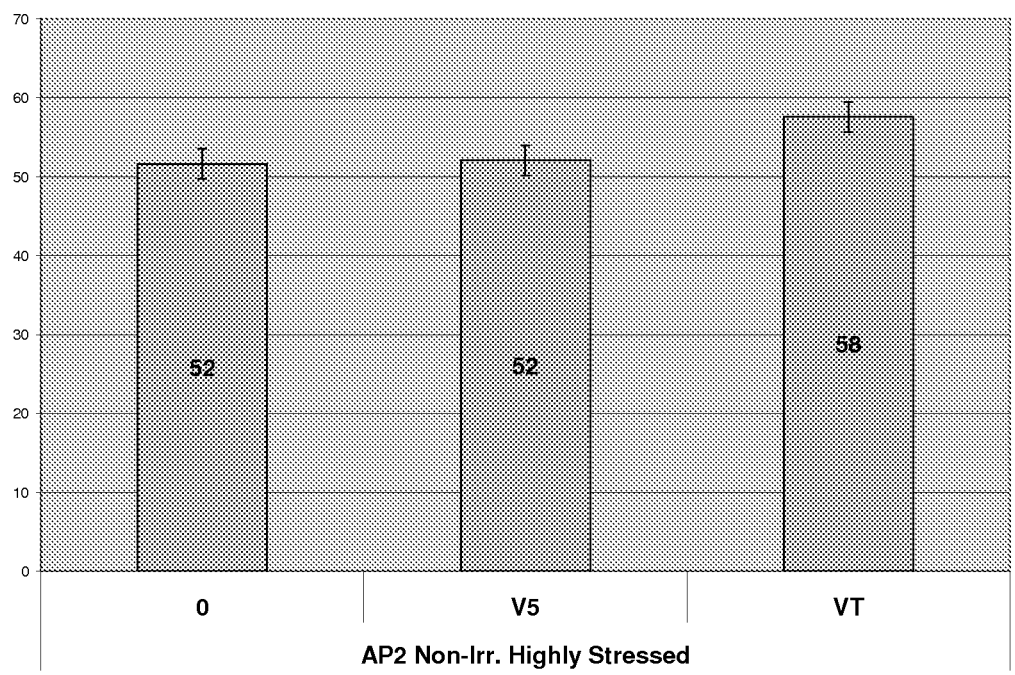
FIG. 3C shows a representative yield comparison between treatments at AP2. Plots treated at the VT timing have increased yield compared to the UTC and the V5 timing although there is no statistical significance.

Yield: A representative yield comparison of trial locations is shown in FIG. 3A. Overall yield of AP2 is significantly reduced due to environmental and biotic stresses during the season. AP2 experienced drought and high temperatures, hail damage and subsequent Japanese beetle infestations. Grain yield at AP1 is very respectable for a seed production field and is enhanced through timely irrigation. A representative yield comparison of treatments across AP1 and AP2 locations is shown in FIG. 3B. Data combined across locations indicate some overall yield reduction though not statistically significant in plots treated compared to the UTC. A representative yield comparison between treatments at AP2 is shown in FIG. 3C. Plots treated at the VT timing have increased yield compared to the UTC and the V5 timing although there is no statistical significance.

Figure 4A:
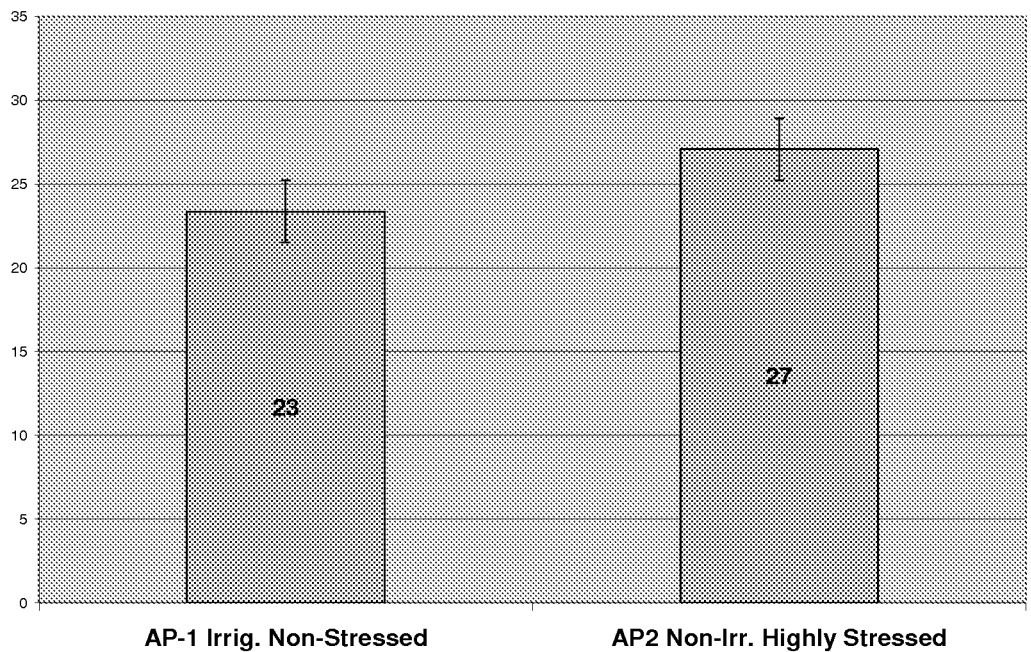
FIG. 4A shows a representative comparison of Grain Moisture at Harvest between AP1 and AP2. Grain at AP2 has significantly higher moisture at harvest than does grain at AP2. Grain harvest is delayed until October 6$^{th}$ (about 3 weeks after seed harvest had occurred). Increased moisture is likely the result of poor plant health and stress.
Figure 4B:
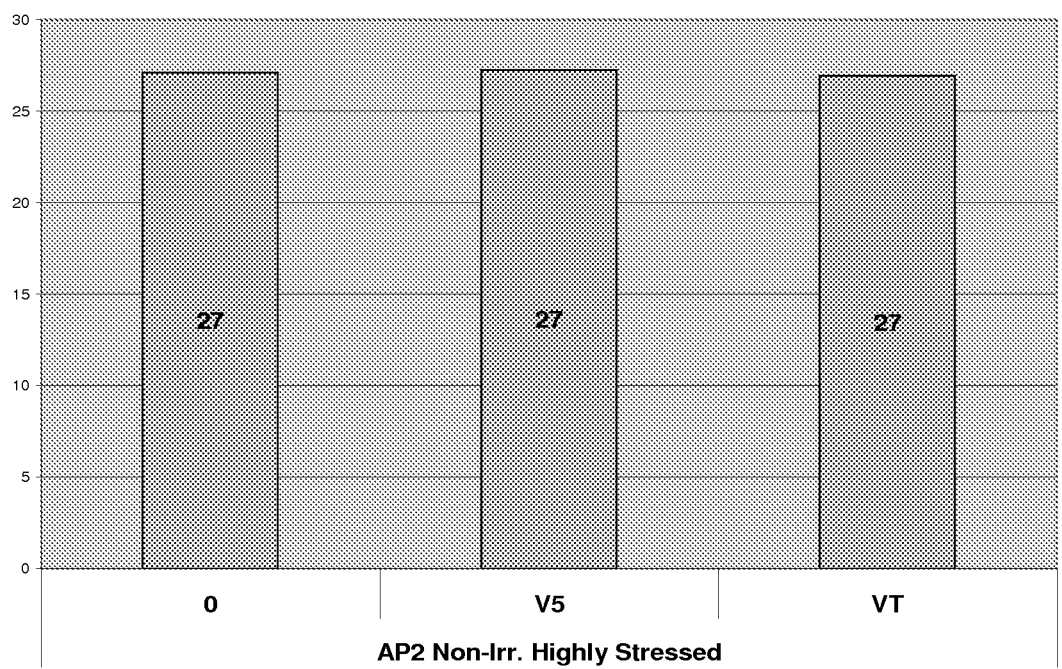
FIG. 4B shows a representative comparison of Grain Moisture between treatments. No difference is observed between treatments for grain moisture.

Grain Moisture at Harvest: A representative comparison of Grain Moisture at Harvest between AP1 and AP2 is shown in FIG. 4A. Grain at AP2 has significantly higher moisture at harvest than does grain at AP2. Grain harvest is delayed until October 6$^{th}$ (about 3 weeks after seed harvest had occurred). Increased moisture is likely the result of poor plant health and stress. A representative comparison of Grain Moisture between treatments is shown in FIG. 4B. No difference is observed between treatments for grain moisture.

Figure 5A:
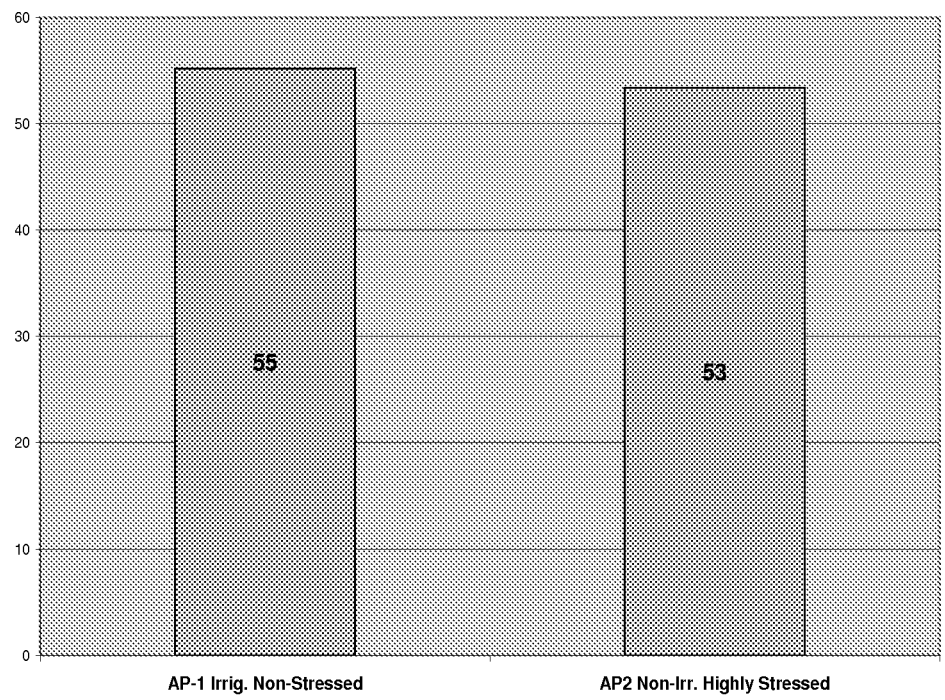
FIG. 5A shows a representative Test Weight comparison between AP1 and AP2. Test weight of grain from AP1 is significantly less than test weight of grain from AP2.
Figure 5B:
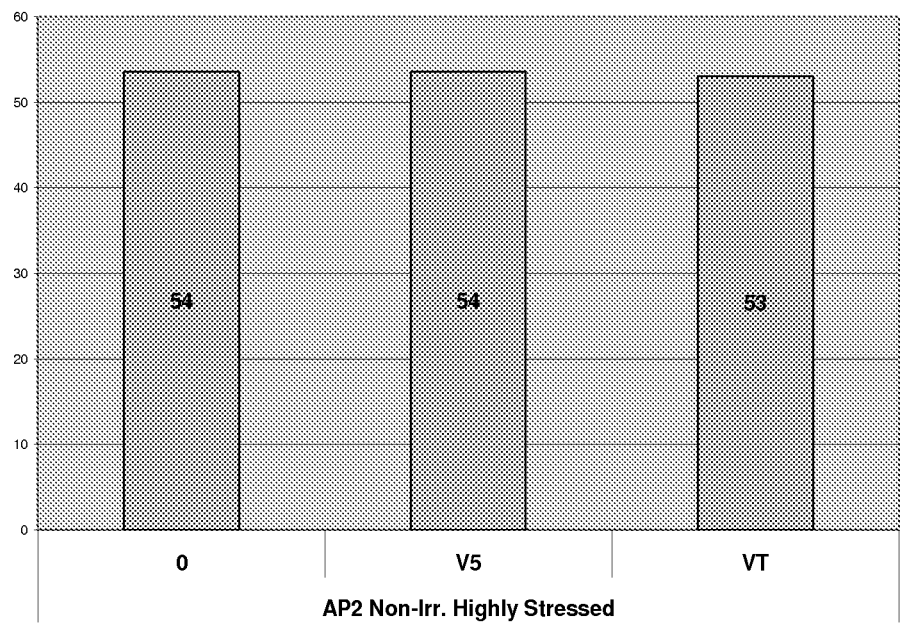
FIG. 5B shows a representative Test Weight Comparison between treatments across locations. There is no significant difference in test weights related to treatments when summarized across locations.
Figure 5C:
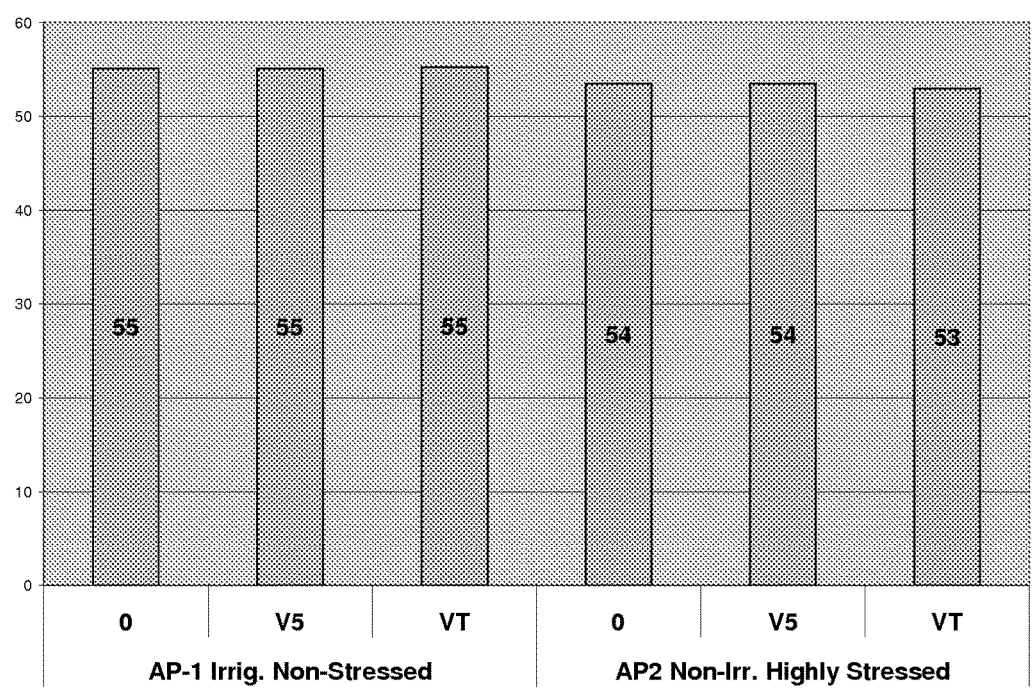
FIG. 5C shows a representative Test weight Comparison between treatments within locations. While at the AP2 location the VT treatment appears to have slightly lower test weight, since only single samples are analyzed from each location, the significance is unknown.

Test Weight and Kernel Weight: A representative Test Weight comparison between AP1 and AP2 is shown in FIG. 5A. Test weight of grain from AP1 is significantly less than test weight of grain from AP2. A representative Test Weight Comparison between treatments across locations is shown in FIG. 5B. There is no significant difference in test weights related to treatments when summarized across locations. A representative Test weight Comparison between treatments within locations is shown in FIG. 5C. While at the AP2 location the VT treatment appears to have slightly lower test weight, since only single samples are analyzed from each location, the significance is unknown.

Figure 6A:
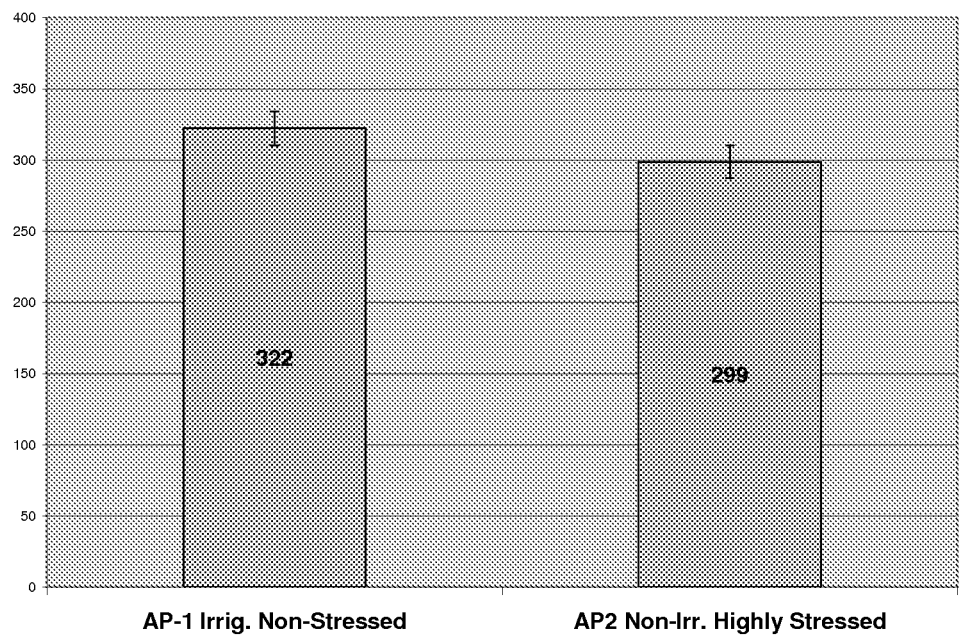
FIG. 6A shows a representative 1000 (1k) Kernel Weight comparison between Locations. Kernel weights of AP1 are significantly greater than those from AP2. Lower kernel weights are probably the result of the stress conditions at AP2.
Figure 6B:
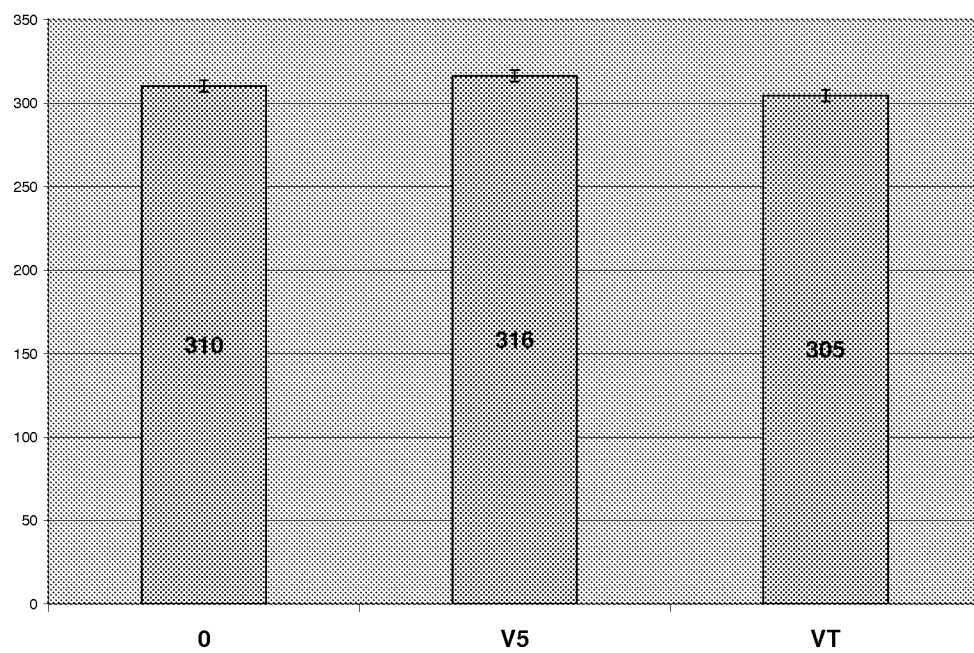
FIG. 6B shows a representative 1000 (1k) Kernel Weight Comparison between Treatments. There are no significant differences in kernel weight related to treatments.
Figure 6C:
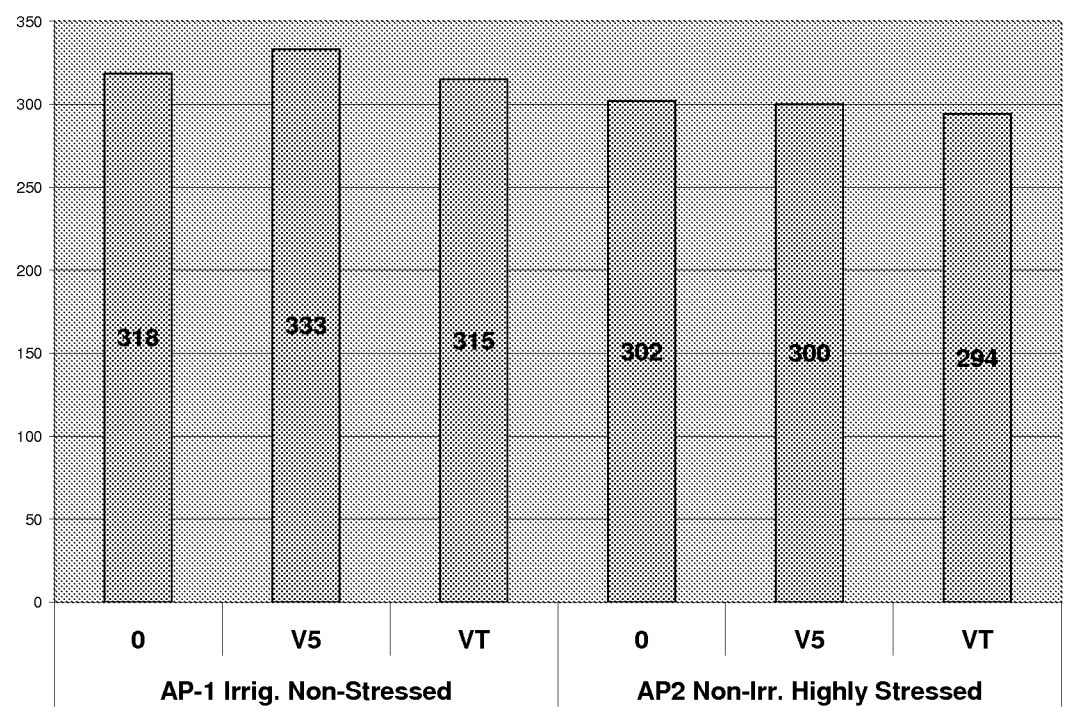
FIG. 6C shows a representative 1000 (1k) Kernel Weight Comparison between Treatments within Locations. Since only single samples are analyzed per location, significance is unknown but there appears to be a trend towards lower kernel weights at AP2 with application of AFxRD-038.

1000 (1k) Kernel Weight: A representative 1000 (1k) Kernel Weight comparison between Locations is shown in FIG. 6A. Kernel weights of AP1 are significantly greater than those from AP2. Lower kernel weights are probably the result of the stress conditions at AP2. A representative 1000 (1k) Kernel Weight Comparison between Treatments is shown in FIG. 6B. There are no significant differences in kernel weight related to treatments. A a representative 1000 (1k) Kernel Weight Comparison between Treatments within Locations is shown in FIG. 6C. Since only single samples are analyzed per location, significance is unknown but there appears to be a trend towards lower kernel weights at AP2 with application of AFxRD-038.

Figure 7A:
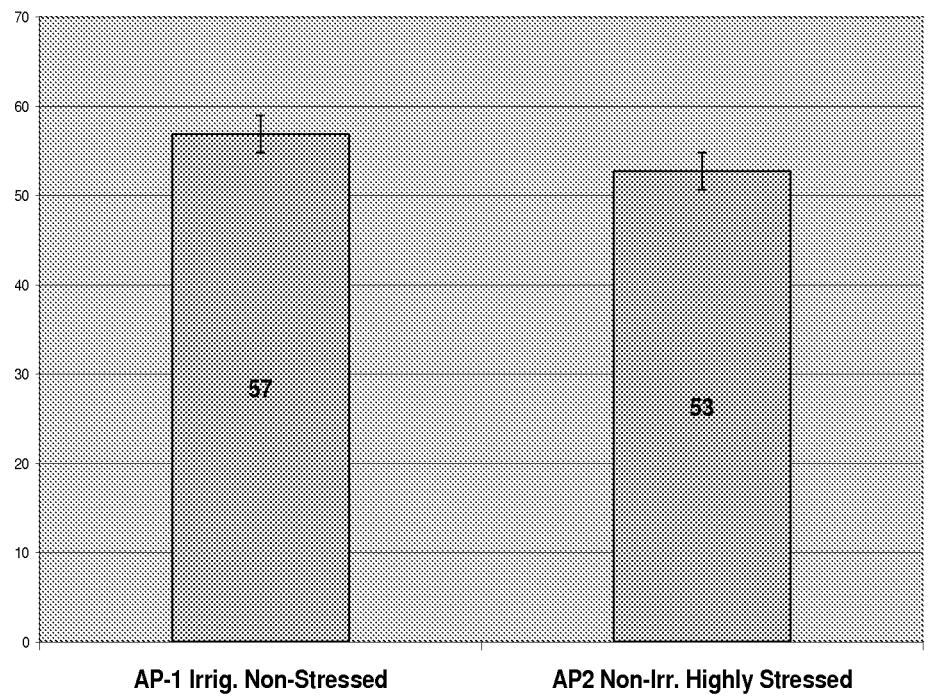
FIG. 7A shows a representative 80K Kernel Bag Weight Comparison between Locations. As expected from the test weight and kernel weights, seed from AP2 is significantly lighter than seed from AP1.
Figure 7B:
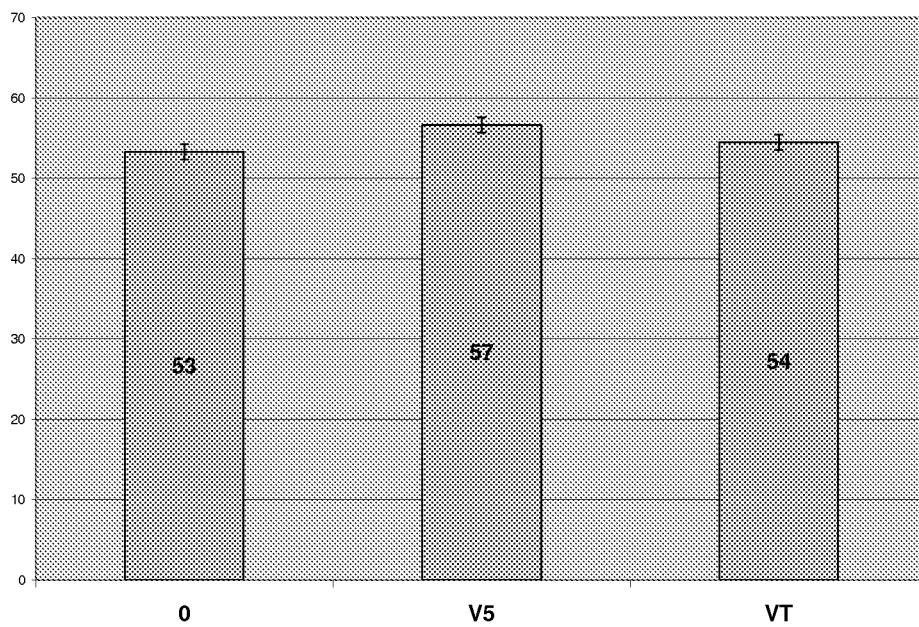
FIG. 7B shows a representative 80k Kernel Bag Weight Comparison between Treatments. There is no significant difference in bag weight related to treatments when summarized across locations.
Figure 7C:
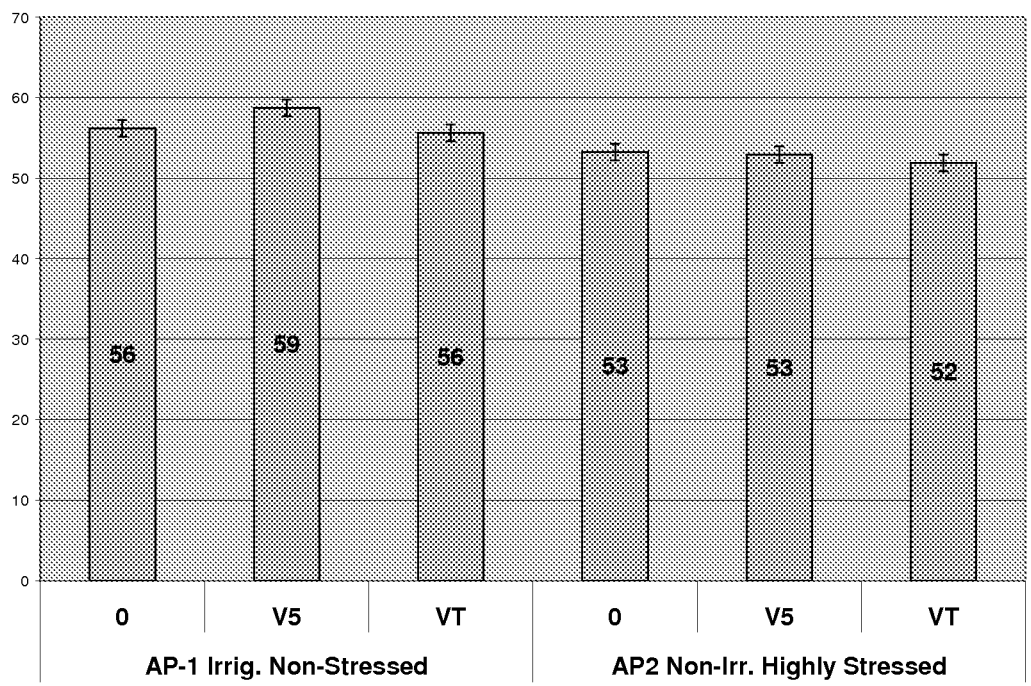
FIG. 7C shows a representative 80k Kernel Bag Weight comparison between treatments within locations. There is no significant difference in bag weight related to treatments.

Weight of 80k Kernel Bag: A representative 80K Kernel Bag Weight Comparison between Locations is shown in FIG. 7A. As expected from the test weight and kernel weights, seed from AP2 is significantly lighter than seed from AP1. A representative 80k Kernel Bag Weight Comparison between Treatments is shown in FIG. 7B. There is no significant difference in bag weight related to treatments when summarized across locations. A representative 80k Kernel Bag Weight comparison between treatments within locations is shown in FIG. 7C. There is no significant difference in bag weight related to treatments.

Figure 8A:
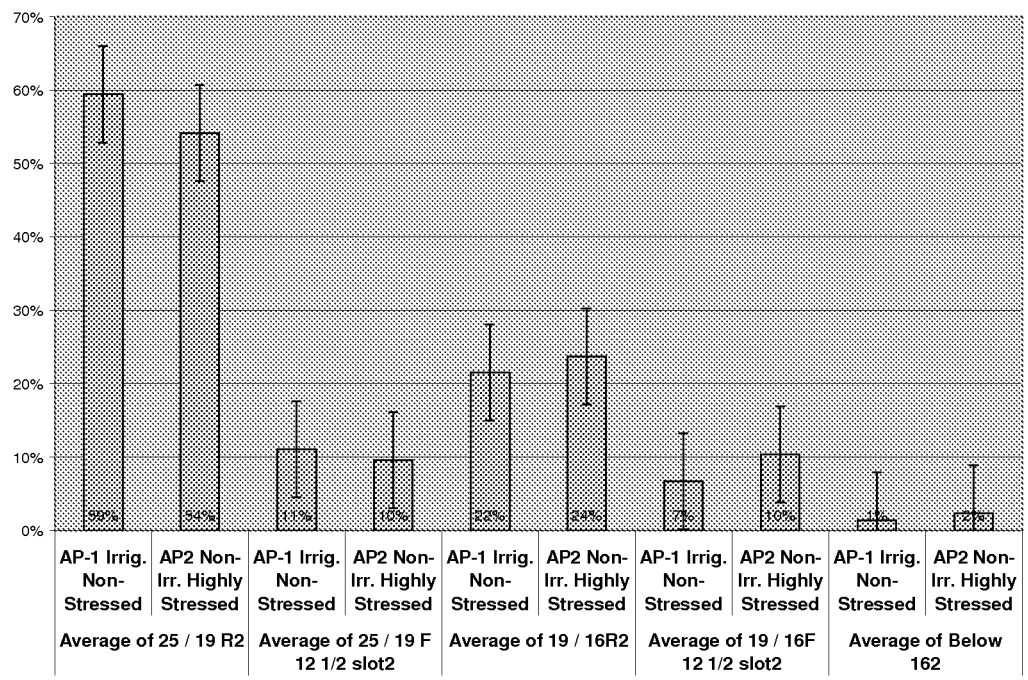
FIG. 8A shows a representative Seed Size Distribution comparison between locations. While not statistically significant, there is a trend toward larger seeds and more round seeds at the AP1 location. The trend is towards more flat seeds at the AP2 location.
Figure 8B:
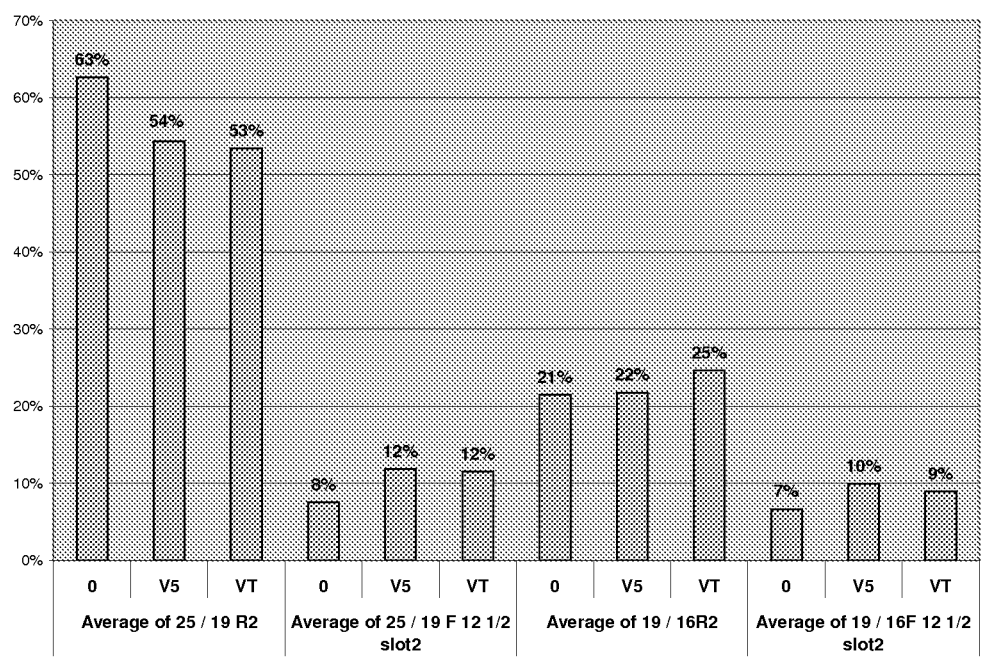
FIG. 8B shows a representative Comparison of Seed Size Distribution as Related to Treatment. While none of the comparisons are statistically significant, there is a trend toward smaller seeds and more flat seeds with applications of AFxRD-038.
Figure 8C:
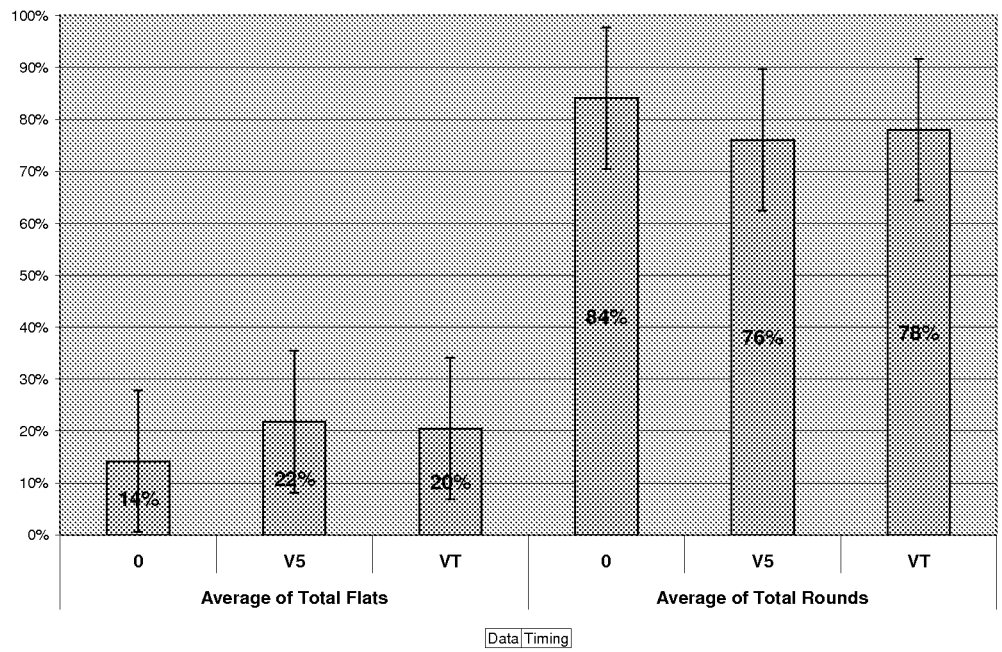
FIG. 8C shows a representative Comparison of Flats versus Rounds between treatments across locations. While not statistically significant, there is a trend toward increased percentage of flat seeds with application of AFxRD-038.
Figure 8D:
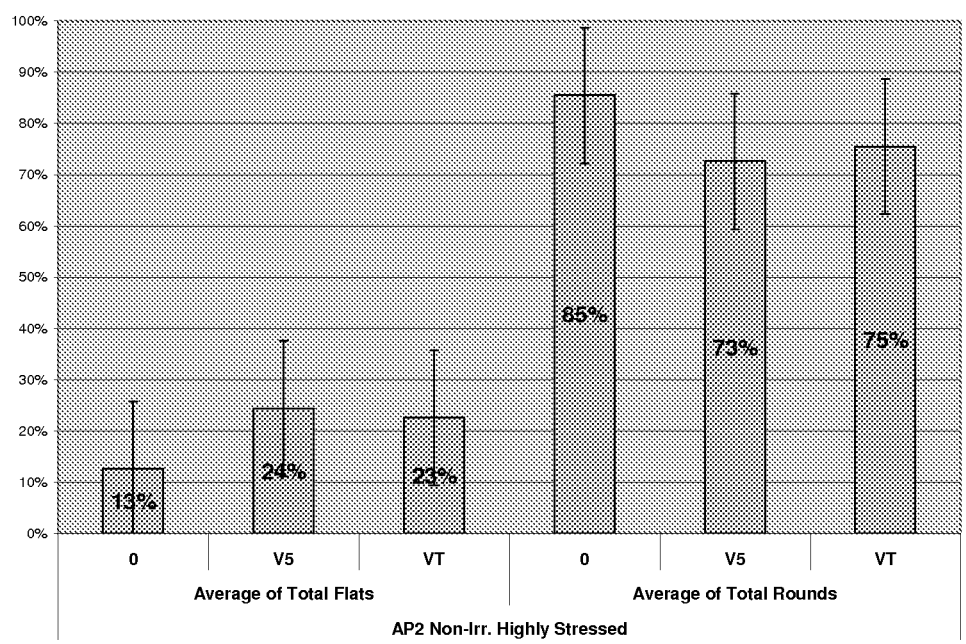
FIG. 8D shows a representative Comparison of Flats versus Rounds within the AP2 location. While not statistically significant, there is a trend toward increased percentage of flat seeds with application of AFxRD-038.

Seed Size Distribution: A representative Seed Size Distribution comparison between locations is shown in FIG. 8A. While not statistically significant, there is a trend toward larger seeds and more round seeds at the AP1 location. The trend is towards more flat seeds at the AP2 location. A representative Comparison of Seed Size Distribution as Related to Treatment is shown in FIG. 8B. While none of the comparisons are statistically significant, there is a trend toward smaller seeds and more flat seeds with applications of AFxRD-038. A representative Comparison of Flats versus Rounds between treatments across locations is shown in FIG. 8C. While not statistically significant, there is a trend toward increased percentage of flat seeds with application of AFxRD-038. A representative Comparison of Flats versus Rounds within the AP2 location is shown in FIG. 8D. While not statistically significant, there is a trend toward increased percentage of flat seeds with application of AFxRD-038.

Figure 9A:
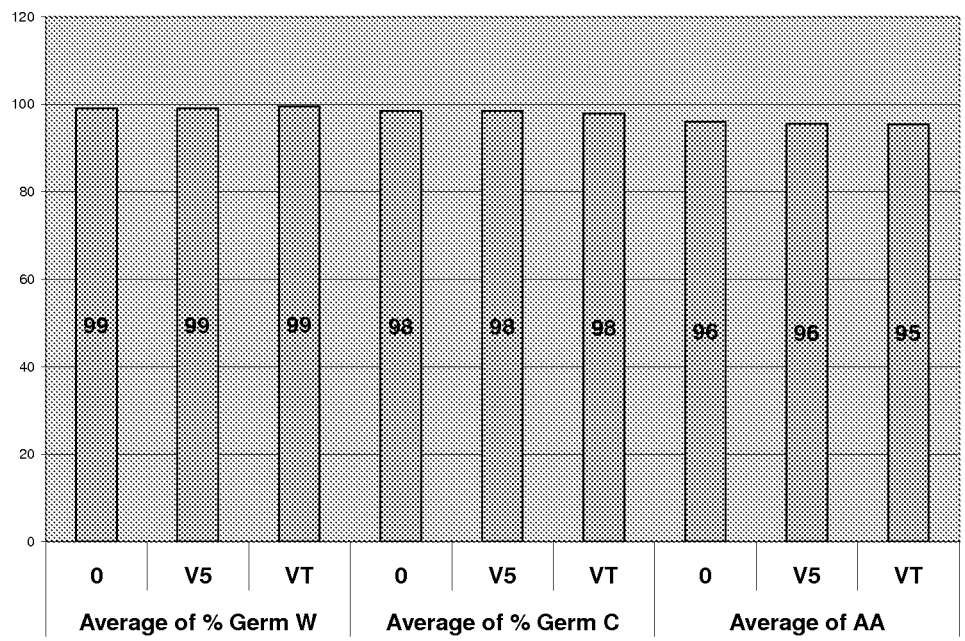
FIG. 9A shows a comparison of Warm, Cold and Advanced Aging % Germination Between Treatments (across locations). There appears to be no effect on germination related to treatment.
Figure 9B:
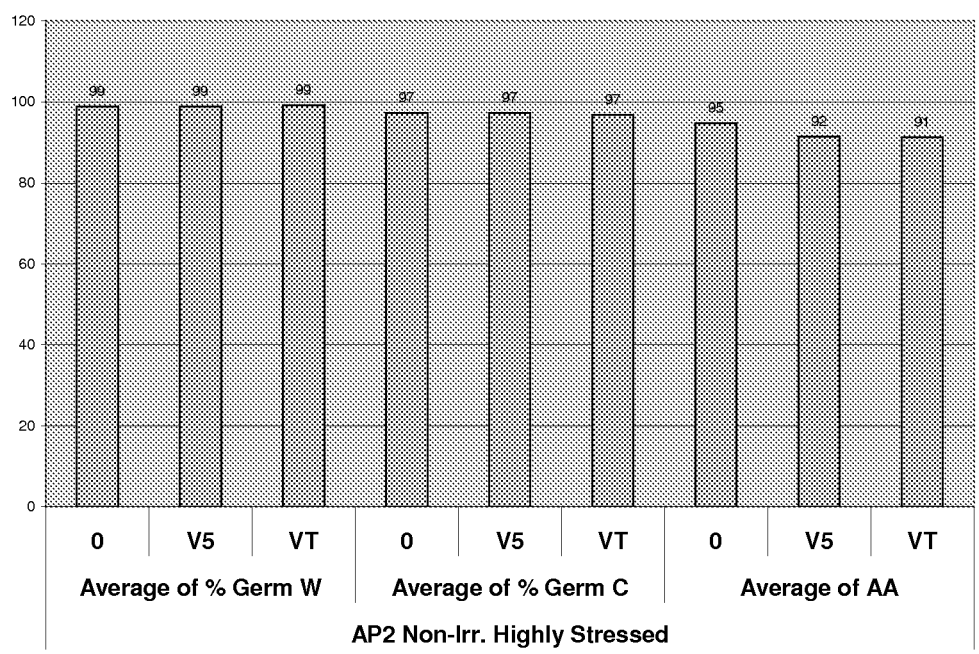
FIG. 9B shows a comparison of Warm, Cold and Advanced Aging % Germination Between Treatments (within locations). There appears to be no effect on warm or cold germination related to treatment at AP2. However, there is possibly a reduction in AA germination with application of AFxRD-038. Only single samples are analyzed per location, so statistical significance is unknown. Also, all germinations are above the critical 90% level required for seed.

Germination: A comparison of Warm, Cold and Advanced Aging % Germination Between Treatments (across locations) is shown in FIG. 9A. There appears to be no effect on germination related to treatment. A comparison of Warm, Cold and Advanced Aging % Germination Between Treatments (within locations) is shown in FIG. 9B. There appears to be no effect on warm or cold germination related to treatment at AP2. However, there is possibly a reduction in AA germination with application of AFxRD-038. Only single samples are analyzed per location, so statistical significance is unknown. Also, all germinations are above the critical 90% level required for seed.

Figure 10A:
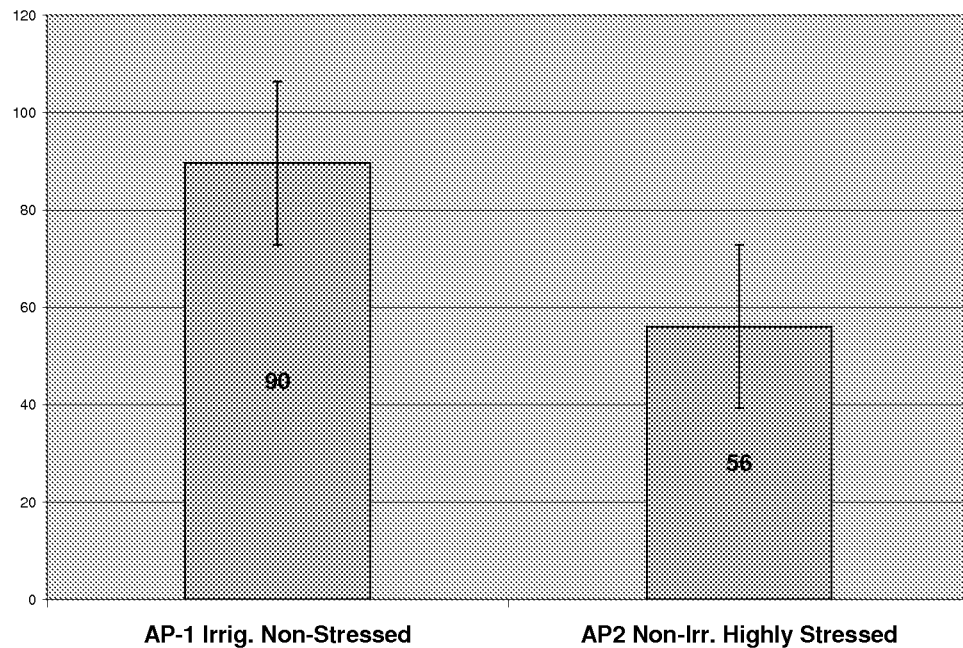
FIG. 10A shows a representative result for Number of saleable units per acre between locations. As expected, there are significantly more saleable units obtained at AP1 (non-stressed) compared to AP2.
Figure 10B:
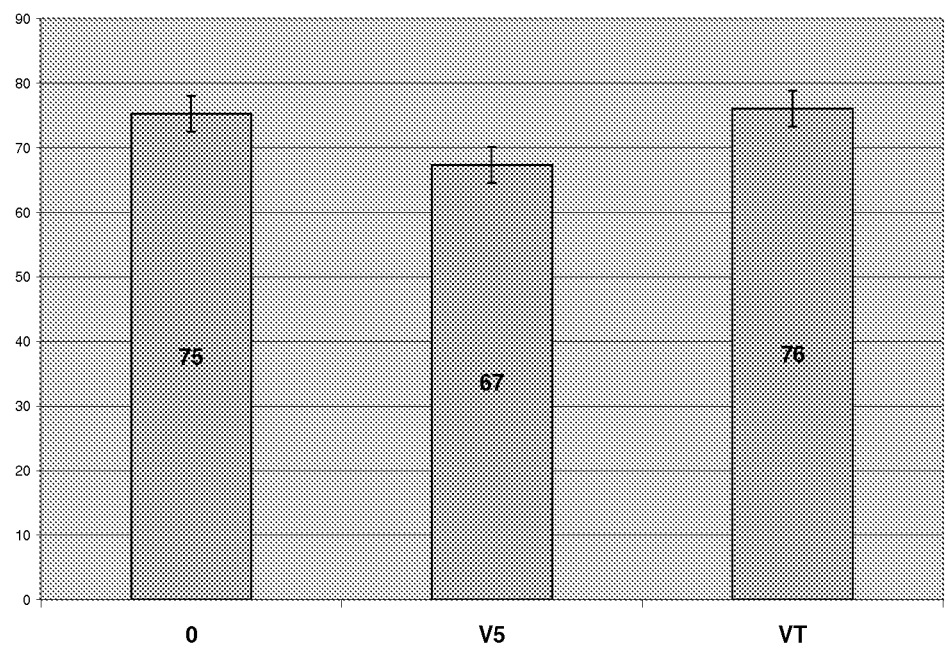
FIG. 10B shows a representative result for Saleable Units versus Treatment (across locations). There is no significant difference in saleable units when comparing treatments across locations.
Figure 10C:
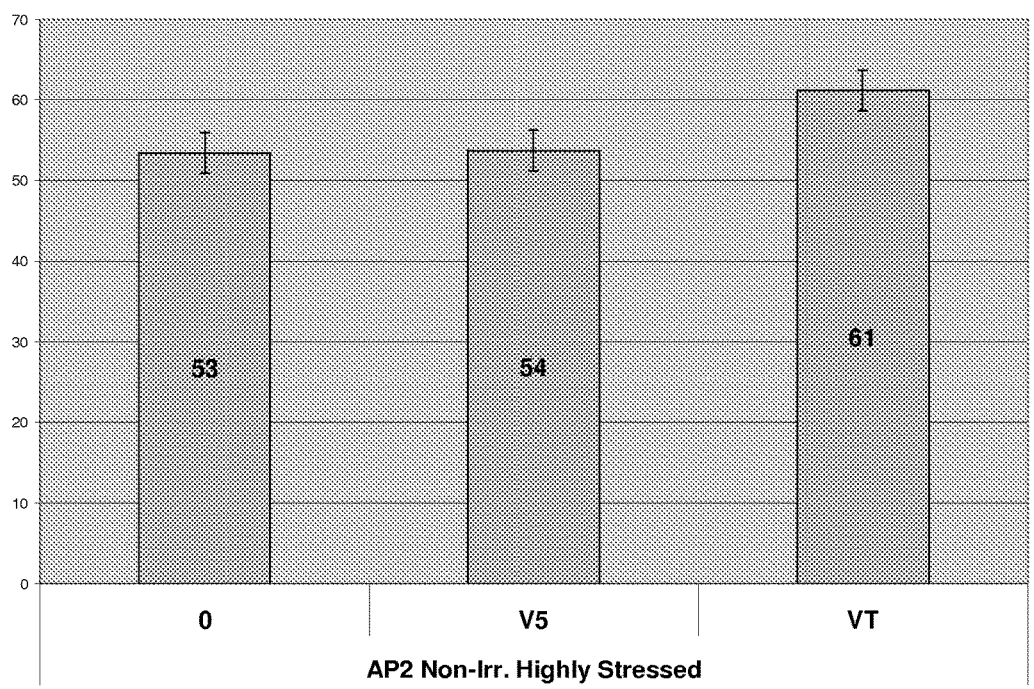
FIG. 10C shows a representative result for Saleable Units versus Treatment at AP2 (stressed location). While not statistically significant, there was nearly a 15% increase of saleable units obtained from the VT application at AP2.

Number of Sellable Units per Acre: A representative result for Number of saleable units per acre between locations is shown in FIG. 10A. As expected, there are significantly more saleable units obtained at AP1 (non-stressed) compared to AP2. A representative result for Saleable Units versus Treatment at AP2 (stressed location) is shown in FIG. 10B. While not statistically significant, there were nearly 15% increase saleable units obtained from the VT application at AP2.

Conclusion: There are no visible phytotoxic effects observed from the applications of AFxRD-038 in any of the plots. There are significant differences in almost all of the seed traits due to location but no statistically significant differences related to treatment. The more stressed location, AP2, resulted in lower yield and fewer, smaller and flatter seeds with slightly lower germination. There are trends towards more flat seeds and more saleable units of seed produced per acre (~15%) with the VT application of AFxRD-038 at the AP2 location. The increase in saleable units seems to be a result of more flats and fewer large round seeds.

I claim:

1. A method for improving yield of a crop produced by a plurality of plants, comprising,
   a) selecting one or more plants of an inbred corn line having increased susceptibility to stress at one or more developmental stages as compared to non-inbred corn plants,
   b) contacting the inbred corn plants with a composition that comprises an effective amount of at least one cyclopropene compound,
   wherein the contacting is performed while the inbred corn plants are in a location other than in a building, the contacting is performed during at least one of said one or more developmental stages,
   c) subsequent to step b), the inbred corn plants are exposed to stress,
   wherein the stress comprises abiotic stress, environmental stress, and mechanical stress, and wherein the mechanical stress comprises detasseling, and
   d) improving the crop yield of the inbred corn plants after being contacted with the effective amount of the at least one cyclopropene compound.

2. The method of claim 1, wherein the composition is a liquid.

3. The method of claim 1, wherein the composition comprises a complex of the cyclopropene compound and a molecular encapsulating agent.

4. The method of claim 1, wherein the at least one cyclopropene compound comprises 1-methylcyclopropene (1-MCP).

5. The method of claim 3, wherein, the molecular encapsulating agent is selected from alpha-cyclodextrin, beta-cyclodextrin, gamma-cyclodextrin, or combinations thereof.

6. The method of claim 1, wherein the environmental stress comprises drought and/or heat.

7. The method of claim 1, wherein the contacting is performed during tassel formation and/or pollination of the crop.

8. The method of claim 1, wherein the contacting is performed during early to mid vegetative growth periods of the crop.

9. The method of claim 1, wherein the yield comprises seed production.

10. The method of claim 1, wherein the yield is improved at least 10%.

11. The method of claim 1, wherein said contacting is performed during a developmental stage selected from the group consisting of V5, V6, V12, VT, and R3.

12. The method of claim 11, wherein the contacting is performed after at least 10% of the inbred corn plants comprising the crop have reached one of V5 or VT growth stages.

13. The method of claim 1, wherein the abiotic stress is selected from a group consisting of dehydration, salinity, high light intensity, low light intensity, high temperature, low temperature, submergence, exposure to heavy metals, oxidative stress, and osmotic stress.

14. The method of claim 13, wherein the abiotic stress is high temperature.

15. The method of claim 12, wherein the contacting is performed after at least 10% of the inbred corn plants comprising the crop have reached the V5 growth stage.

16. The method of claim 12, wherein the contacting is performed after at least 10% of the inbred corn plants comprising the crop have reached the VT growth stage.

17. The method of claim 16, wherein the yield comprises an increased number of flat seeds.

18. The method of claim 17, wherein the increased number of flat seeds of the yield produced an increased number of saleable units of seeds.

19. The method of claim 18, wherein the yield comprises about 15% of an increased number of saleable units of seeds.

20. The method of claim 9, wherein no phytotoxic effects were observed on seed production.

* * * * *